(12) United States Patent
Brekke et al.

(10) Patent No.: US 10,744,230 B2
(45) Date of Patent: Aug. 18, 2020

(54) BIOMIMETIC HYBRID GEL COMPOSITIONS AND METHODS OF USE

(71) Applicants: BIOACTIVE REGENERATIVE THERAPEUTICS, INC., Two Harbors, MN (US); REGENTS OF THE UNIVERSITY OF MINNESOTA, Minneapolis, MN (US)

(72) Inventors: John H. Brekke, Two Harbors, MN (US); Timothy O'Brien, Minneapolis, MN (US)

(73) Assignees: BIOACTIVE REGENERATIVE THERAPEUTICS, INC., Two Harbors, MN (US); REGENTS OF THE UNIVERSITY OF MINNESOTA, Minneapolis, MN (US)

(*) Notice: Subject to any disclaimer, the term of this patent is extended or adjusted under 35 U.S.C. 154(b) by 82 days.

(21) Appl. No.: 15/968,084

(22) Filed: May 1, 2018

(65) Prior Publication Data
US 2018/0250443 A1 Sep. 6, 2018

Related U.S. Application Data

(62) Division of application No. 15/023,843, filed as application No. PCT/US2014/058397 on Sep. 30, 2014, now Pat. No. 9,981,067.
(Continued)

(51) Int. Cl.
*A61L 27/54* (2006.01)
*A61K 9/00* (2006.01)
(Continued)

(52) U.S. Cl.
CPC ............ *A61L 27/54* (2013.01); *A61K 9/0024* (2013.01); *A61K 35/28* (2013.01); *A61K 35/30* (2013.01);
(Continued)

(58) Field of Classification Search
None
See application file for complete search history.

(56) References Cited

U.S. PATENT DOCUMENTS

| 5,133,755 A | 7/1992 | Brekke |
| 5,166,187 A | 11/1992 | Collombel et al. |
| (Continued) | | |

FOREIGN PATENT DOCUMENTS

| EP | 0544259 A1 | 6/1993 |
| EP | 0640647 A2 | 3/1995 |
| (Continued) | | |

OTHER PUBLICATIONS

Balazs, Medical Applications of Hyaluronan and its Derivatives, Cosmetic and Pharmaceutical Application of Polymers (1991), pp. 293-310.
(Continued)

*Primary Examiner* — David W Berke-Schlessel
(74) *Attorney, Agent, or Firm* — Troutman Pepper Hamilton Sanders LLP

(57) ABSTRACT

Disclosed herein are dry blends of polyanionic and polycationic macromolecules, solvating fluids serving as cell suspension fluids, hybrid gel compositions, and methods for treatment of patients with endocrine disorders by transplantation with such compositions. Hybrid gel compositions that promote a microenvironment suitable for cell viability and growth while maintaining a sufficient structural integrity for three-dimensional cell culture are also disclosed.

18 Claims, 5 Drawing Sheets
Specification includes a Sequence Listing.

Related U.S. Application Data

(60) Provisional application No. 61/884,945, filed on Sep. 30, 2013.

(51) Int. Cl.

| | | |
|---|---|---|
| *A61K 35/55* | (2015.01) | |
| *A61K 35/39* | (2015.01) | |
| *A61K 35/28* | (2015.01) | |
| *A61K 35/30* | (2015.01) | |
| *A61L 27/26* | (2006.01) | |
| *A61L 27/38* | (2006.01) | |
| *A61L 27/52* | (2006.01) | |
| *A61K 47/36* | (2006.01) | |
| *A61K 45/06* | (2006.01) | |

(52) U.S. Cl.
CPC .............. *A61K 35/39* (2013.01); *A61K 35/55* (2013.01); *A61K 45/06* (2013.01); *A61K 47/36* (2013.01); *A61L 27/26* (2013.01); *A61L 27/3804* (2013.01); *A61L 27/3834* (2013.01); *A61L 27/3886* (2013.01); *A61L 27/52* (2013.01); *A61L 2300/236* (2013.01); *A61L 2300/252* (2013.01)

(56) References Cited

U.S. PATENT DOCUMENTS

| | | |
|---|---|---|
| 5,306,311 A | 4/1994 | Stone et al. |
| 5,486,359 A | 1/1996 | Caplan et al. |
| 6,060,410 A | 5/2000 | Gillberg-LaForce et al. |
| 6,156,572 A | 12/2000 | Bellamkonda et al. |
| 6,482,231 B1 | 11/2002 | Abatangelo et al. |
| 6,596,274 B1 | 7/2003 | Abatangelo et al. |
| 7,393,919 B2 | 7/2008 | Levetan et al. |
| 7,524,514 B2 | 4/2009 | Brekke |
| 8,137,696 B2 | 3/2012 | Brekke |
| 2002/0032488 A1 | 3/2002 | Brekke et al. |
| 2004/0006146 A1 | 1/2004 | Evans et al. |
| 2005/0214341 A1 | 9/2005 | Brekke |
| 2007/0100015 A1 | 5/2007 | Hubbell |
| 2009/0238874 A1 | 9/2009 | Brekke |
| 2011/0129919 A1 | 6/2011 | Oh et al. |
| 2013/0005681 A1 | 1/2013 | Su et al. |
| 2013/0189371 A1 | 7/2013 | Lamberti et al. |
| 2016/0213817 A1 | 7/2016 | Brekke et al. |

FOREIGN PATENT DOCUMENTS

| | | |
|---|---|---|
| EP | 0784985 A1 | 7/1997 |
| EP | 1003567 B1 | 8/2003 |
| EP | 2233144 A1 | 9/2010 |
| EP | 1702064 B1 | 5/2012 |
| WO | 1999007416 A1 | 2/1999 |
| WO | 2000002600 A1 | 1/2000 |
| WO | 2002030480 A1 | 4/2002 |
| WO | 2003008007 A2 | 1/2003 |
| WO | 2004006973 A1 | 1/2004 |
| WO | 2004029095 A2 | 4/2004 |
| WO | 2005054110 A2 | 6/2005 |
| WO | 2015048774 A2 | 4/2015 |

OTHER PUBLICATIONS

Beresford, Osteogenic Stem Cells and the Stromal System of Bone and Marrow, Clin. Orthop. Relat. Res. (Mar. 1989), 240:270-280.

Bianco et al., Bone Marrow Stromal Stem Cells: Nature, Biology, and Potential Applications, Stem Cells (2001), 19:180-192.

Blagosklonny et al., Molecular Effects of Paclitaxel: Myths and Reality (A Critical Review), Int. J. Cancer (1999), 83:151-156.

Boddohi et al., Polysaccharide-Based Polyelectrolyte Complex Nanoparticles from Chitosan, Heparin, and Hlyaluronan, Biomacromolecules (2009), 10(6):1402-1409.

Deb et al., Bone Marrow-Derived Cardiomyocytes Are Present in Adult Human Heart: A Study of Gender-Mismatched Bone Marrow Transplantation Patients, Circulation (Mar. 11, 2003), 107(9):1247-1249.

Demarger-Andre et al., Chitosan Carboxylic Acid Salts in Solution and in the Solid State, Carbohydrate Polymers (1994), 23(3):211-219.

Denuziere et al., Chitosan-Chondroitin Sulfate and Chitosan-Hyaluronate Polyelectrolyte Complexes: Biological Properties, Biomaterials (Jul. 1998),19(14):1275-1285.

Denuziere et al., Chitosan-Chondroitin Sulfate and Chitosan-Hyaluronate Polyelectrolyte Complexes. Physico-Chemical Aspects, Carbohydrate Polymers (Apr. 1996), 29(4):317-323.

Denuziere et al., Interactions Between Chitosan and Glycosaminoglycans (Chondroitin Sulfate and Hyaluronic Acid): Physicochemical and Biological Studies, Annales Pharmaceutiques Francaises (Feb. 2000), 58(11:47-53.

Supplementary European Search Report dated Mar. 27, 2008 for EP 04812547.

Supplementary European Search Report dated Mar. 22, 2017 for EP 14847112.

Frenkel et al., Regeneration of Articular Cartilage—Evaluation of Osteochondral Defect Repair in the Rabbit Using Multiphasic Implants, Osteoarthritis and Cartilage (Sep. 2005), 13(9):798-807.

Hardingham et al., The Specific Interaction of Hyaluronic Acid With Cartilage Proteoglycans, Biochimica et Biophysica Acta (BBA)—General Subjects (Sep. 15, 1972), 279(2):401-405.

Hoffman, Hydrogels for Biomedical Applications, Advanced Drug Delivery Reviews (Jan. 17, 2002), 54(1):3-12.

Hung et al., Isolation and Characterization of Size-Sieved Stem Cells from Human Bone Marrow, Stem Cells (2002), 20:249-258.

Ingber, Tensegrity I. Cell Structure and Hierarchical Systems Biology, Journal of Cell Science (2003), 116:1157-1173.

Ingber, The Architecture of Life, Scientific American (Feb. 1998), 278(1):48-57.

International Search Report dated Aug. 12, 2005 for PCT/US2004/040051.

International Search Report and Written Opinion dated Mar. 24, 2015 for PCT/US2014/058397.

Kabanov et al., A New Class of Complex Water-Soluble Polyelectrolytes, Macromolecular Chemistry and Physics (Mar. 1984), 6(6):259-276.

Kekkonen et al., Adsorption Kinetics of Complexes Formed by Oppositely Charged Polyelectrolytes, Journal of Colloid and Interface Science (Feb. 15, 2001), 234(2):384-392.

Knudson, Hyaluronan Receptor-directed Assembly of Chondrocyte Pericellular Matrix, Journal of Cell Biology (Feb. 1993), 120(3):825-834.

Kvam et al., Purification and Characterization of Hyaluronan from Synovial Fluid, Analytical Biochemistry (May 15, 1993), 211(1):44-49.

Larsen et al., Effect of Hylan on Cartilage and Chondrocyte Cultures, Journal of Orthopaedic Research (Jan. 1992), 10(1):23-32.

Lin et al., pH-Sensitive Polyelectrolyte Complex Gel Microspheres Composed of Chitosan/Sodium Tripolyphosphate/Dextran Sulfate: Swelling Kinetics and Drug Delivery Properties, Colloids and Surfaces B: Biointerfaces (Aug. 2005), 14(2-3):143-151.

Lindborg et al., Rapid Induction of Cerebral Organoids From Human Induced Pluripotent Stem Cells Using a Chemically Defined Hydrogel and Defined Cell Culture Medium, Stem Cells Translational Medicine (Jul. 2016), 5(7):1-10.

Lee et al., Preparation and Properties of Polyelectrolyte Complex Sponges Composed of Hyaluronic Acid and Chitosan and Their Biological Behaviors, Journal of Applied Polymer Science (Oct. 24, 2003), 90(4):925-932.

Luo et al., Cross-Linked Hyaluronic Acid Hydrogel Films: New Biomaterials for Drug Delivery, Journal of Controlled Release (Oct. 3, 2000), 69(1):169-184.

Luo et al., Synthesis and Selective Cytotoxicity of a Hyaluronic Acid-Antitumor Bioconjugate, Bioconjugate Chemistry (1999), 10(5):755-763.

(56) References Cited

OTHER PUBLICATIONS

Morgelin et al., Assembly of Cartilage Proteoglycan with Hyaluronate and Structure of the Central Filament in Proteoglycan Aggregate, Biochemical Society Transactions (Apr. 1, 1990), 18(2):204-207.

Muzzarelli et al., Antimicrobial Properties of N-carboxybutyl Chitosan, Antimicrobial Agents and Chemotherapy (Oct. 1990), 34(10):2019-2023.

Neame et al., The Link Proteins, Experientia 49 (1994), pp. 393-402.

Brockop et al., One Strategy for Cell and Gene Therapy: Harnessing the Power of Adult Stem Cells to Repair Tissues, PNAS (Sep. 30, 2003), 100(1):11917-11923.

Sakiyama et al., pH-Sensitive Shrinking of a Dextran Sulfate/Chitosan Complex Gel and Its Promotion Effect on the Release of Polymeric Substances, Journal of Applied Polymer Science (May 3, 2001), 81(3):667-674.

Sottile et al., Stem Cell Characteristics of Human Trabecular Bone-Derived Cells, Bone (May 2002), 30(5):699-704.

Suh et al., Application of Chitosan-Based Polysaccharide Biomaterials in Cartilage Tissue Engineering: A Review, Biomaterials (Dec. 15, 2000), 21(24):2589-2598.

Takayama et al., Effect of Interpolymer Complex Formation on Bioadhesive Property and Drug Release Phenomenon of Compressed Tablet Consisting of Chitosan and Sodium Hyaluronate, Chemical and Pharmaceutical Bulletin (1990), 38(7):1993-1997.

Tan et al., Evaluation of Nanostructured Composite Collagen—Chitosan Matrices for Tissue Engineering, Tissue Engineering (Apr. 2001), 7(2):203-210.

Tateishi-Yuyama et al., Therapeutic Angiogenesis for Patients With Limb Ischaemia by Autologous Transplantation of Bone-Marrow Cells: A Pilot Study and a Randomised Controlled Trial, The Lancet (Aug. 10, 2002),360(9331):427-435.

Vercruysse et al., Synthesis and in Vitro Degradation of New Polyvalent Hydrazide Cross-Linked Hydrogels of Hyaluronic Acid, Bioconjugate Chemistry (Sep. 25 1997), 8(5):686-694.

Yan et al., PEC Films Prepared from Chitosan-Alginate Coacervates, Chemical and Pharmaceutical Bulletin (2000), 48(7):941-946.

Yeh et al., Tissue Engineered Neocartilage Using Chitosan Gel and Chondrocytes, Tissue Engineering (Dec. 1, 2002), 8(6):1197(pp. 72).

Yu et al., Surface Modification of Poly(Tetramethylene Adipate-Co-Terephthalate) Membrane via Layer-By-Layer Assembly of Chitosan and Dextran Sulfate Polyelectrolyte Multiplayer, Colloids and Surfaces B: Biointerfaces (Feb. 15, 2007), 54(2):222-229.

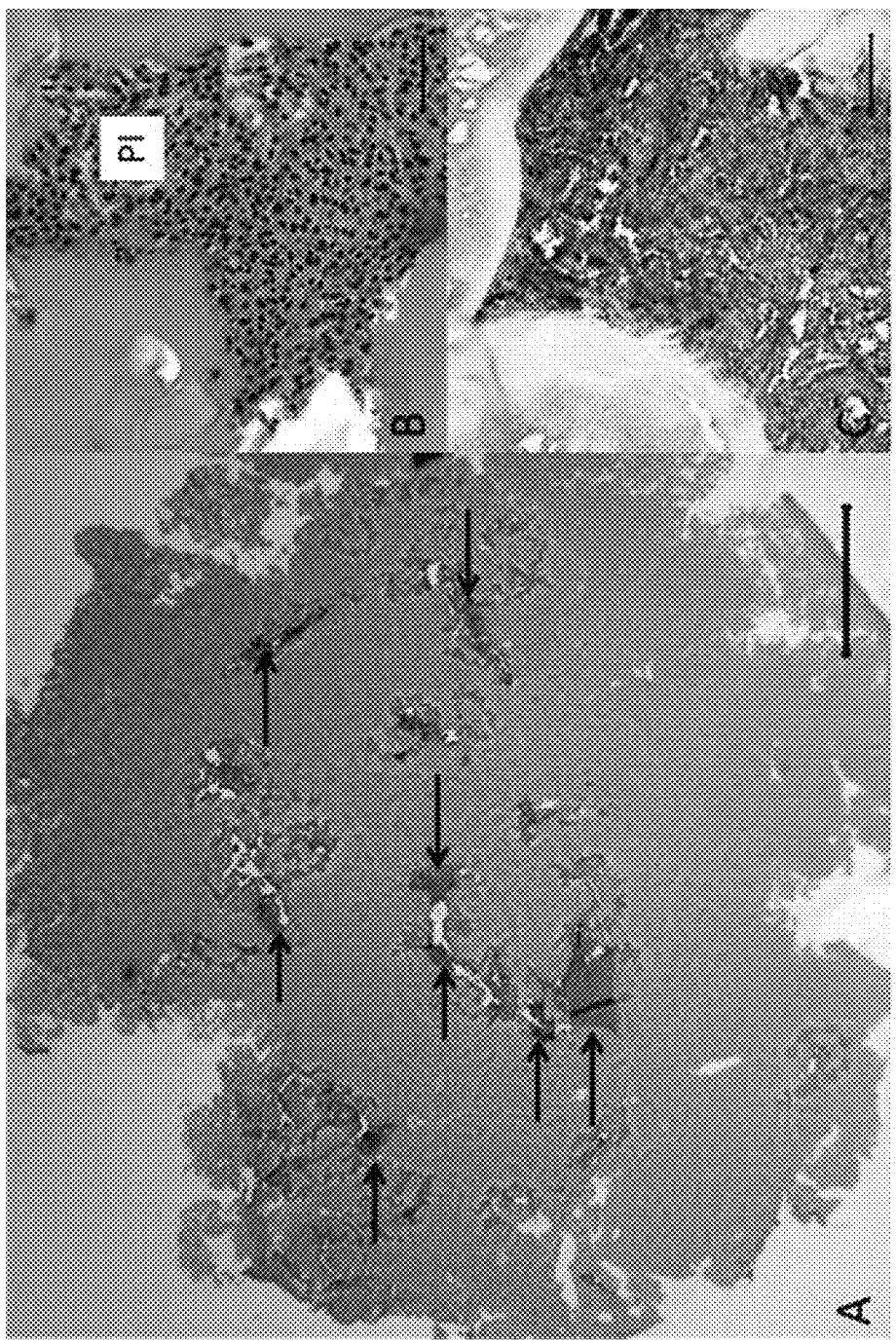
FIGURE 3A-C

FIGURE 4

|   | Sample ID | C-Peptide (ng/mL) | Assay Date | Sample Type | Received in lab |
|---|---|---|---|---|---|
| 1 | 1 free pig islets D1, 4/25/13 | >1000 | 7/15/2013 | media | 5/2/2013 |
| 2 | 2 free pig islets D2 | >1000 | 7/15/2013 | media | 5/2/2013 |
| 3 | 3 free pig islets D5 | >1000 | 7/15/2013 | media | 5/2/2013 |
| 4 | 4 free pig islets D7 | >1000 | 7/15/2013 | media | 5/2/2013 |
| 5 | 5 HGC pig islets D1 | 792.00 | 7/15/2013 | media | 5/2/2013 |
| 6 | 6 HGC pig islets D2 | 240.00 | 7/15/2013 | media | 5/2/2013 |
| 7 | 7 HGC pig islets D5 | 460.00 | 7/15/2013 | media | 5/2/2013 |
| 8 | 8 HGC pig islets D7 | 115.00 | 7/15/2013 | media | 5/2/2013 |
| 9 | 9 media blank control | 0.16 | 6/25/2013 | media | 5/2/2013 |

BIOMIMETIC HYBRID GEL COMPOSITIONS AND METHODS OF USE

CROSS-REFERENCE TO RELATED APPLICATIONS

This application is a divisional application of U.S. application Ser. No. 15/023,843, entitled "Biomimetic Hybrid Gel Compositions And Methods Of Use," filed Mar. 22, 2016, which is a U.S. national stage filing under 35 U.S.C. § 371 of International Application No. PCT/US2014/058397 entitled "Biomimetic Hybrid Gel Compositions And Methods Of Use," and filed on Sep. 30, 2014, which claims the benefit of and priority under 35 U.S.C. § 119(e) to U.S. Provisional Application No. 61/884,945 entitled "Biomimetic Therapeutic Hydrocolloids, Hybrid Hydrocolloid/Hydrogels And Methods Of Use," filed Sep. 30, 2013. The contents of each of these applications are hereby incorporated herein by reference in their entireties.

SUMMARY

The fields of regenerative medicine and tissue engineering focus on repairing and regenerating tissue lost or damaged due to injury, disease, or congenital anomalies. Effective regenerative medicine constructs can be created when knowledge of healthy tissue composition, organization (at cellular and molecular levels), and complex biologic functions are joined to knowledge of biomimetic materials and integrated with therapeutic advantages provided by various cell phenotypes and soluble signaling factors. Chemical, structural, mechanical, and biologic properties of such materials can be controlled to provide customized, biomimetic microenvironments within which populations of pluripotent cells can expand and differentiate to therapeutically useful phenotypes. In the alternative, collections of fully differentiated and metabolically active cells may be embedded within these materials, functioning as transplantation platforms, for cell delivery to damaged tissue sites and integration of the whole into the host organism.

Various polymers, such as polyacrylamides, polyethylene glycol, polyvinyl alcohol, agarose, poly (α-hydroxy acids), methylcellulose, and chemically cross-linked hyaluronan (to name only a few) have been used in attempts to create materials with properties described above. However, these compositions have not been able to provide all the qualities required of a biomimetic microenvironment while also being biocompatible and biologically relevant to their cell cargos and/or intended host tissues. Thus, there is a need for improved cell culture and transplantation materials whose components provide: (i) three-dimensional (3D) architecture, (ii) structural and mechanical properties appropriate for embedded cells and target tissue, (iii) directed phenotypic support for the embedded cells, (iv) a reservoir for soluble signaling molecules, (v) protection for the embedded cells from recognition by innate and acquired immune systems of the host organism, and (vi) protection for embedded cells from effects of autocrine and paracrine generated apoptotic cytokines.

Disclosed herein are compositions for creating biocompatible, biomimetic, and biologically relevant compositions for three-dimensional in vitro cultures of cells as well as transplantation of cells in vivo. Such compositions are adapted to provide customized microenvironments within which pluripotent and/or therapeutic cell types may be embedded. Compositions that promote a microenvironment suitable for endocrine cell viability and growth, while maintaining prescribed structural and mechanical properties as well as protection from immune system attack, are also disclosed.

In some embodiments, the disclosed compositions may have a plurality of polyanionic macromolecules and a plurality of polycationic macromolecules. In other embodiments, the composition may include a solvating fluid to form a hybrid gel composition. In other embodiments, the compositions may include dextran sulfate (a polyanionic macromolecule), at least one polycationic macromolecule, and a solvating fluid. The composition may be a fully hydrated construct. In other embodiments, the composition may be a hybrid gel composition. In further embodiments, the compositions may include a glycosaminoglycan, such as hyaluronan, operating independently as a polyanionic macromolecule or as a companion (polyanionic macromolecule) to dextran sulfate. Yet other embodiments may include biologically active peptides, extracellular matrix glycoproteins (e.g. laminin, fibronectin, osteonectin), proteoglycans (e.g. aggrecan, chondroitin sulfate proteoglycan 2, neurocan), and/or additional glycosaminoglycans (e.g. chondroitin sulfate, dermatan sulfate, heparan sulfate, and keratan sulfate).

In some embodiments, the plurality of polyanionic macromolecules and plurality of polycationic macromolecules may be anhydrous. In other embodiments, the polyanionic macromolecule may be dissolved in a buffered, solvating fluid prior to its introduction to the polycationic macromolecule existing as dry particles. Disclosed compositions and methods provide hybrid gel compositions that create biocompatible microenvironments with improved structural and mechanical properties as well as biologic properties relevant to specific cell types and target tissues. In some embodiments, the hybrid gel composition, embedded with cells, may be studied in vitro as a three-dimensional, cell culture system. In certain embodiments in which the composition functions as a cell transplantation platform, dextran sulfate is used as the polyanionic macromolecule and introduced to the dry polycationic macromolecule via the solvating fluid together with cells suspended in the solvating fluid. It is believed that dextran sulfate provides the fully formed construct with multiple, disparate attributes such as: (i) protection of the cell cargo from attack by the host organism's innate and acquired immune systems and recognition by its complement system, (ii) protection of the transplant system against fibrosis by functioning as an anticoagulant at the construct's exposed surfaces, and (iii) establishing physiologic osmolarity for the cells' microenvironment, in conjunction with a solvating fluid.

In some embodiments, a method for forming a hybrid gel composition is disclosed. The method may comprise combining anhydrous dextran sulfate and a solvating fluid to form a composition, and adding at least one polycationic macromolecule to the composition to form a hybrid gel composition, wherein a network of insoluble, polyelectrolytic complex structures that surround and penetrate regions of unreacted, homogeneous, dextran sulfate and other regions of unreacted, homogeneous polycationic macromolecules is formed. In other embodiments, the method may combine anhydrous dextran sulfate and an anhydrous polycationic macromolecule, wherein a dry mixture is created, and hydrating this dry mixture with a solvating fluid wherein a network of insoluble, polyelectrolytic complex (PEC) structures that surround and penetrate regions of unreacted, homogeneous, dextran sulfate and other regions of unreacted, homogeneous polycationic macromolecules is formed.

Some embodiments herein describe methods of treating an endocrine disorder in a patient comprising administering to the patient a hybrid gel composition described in embodiments herein. In other embodiments, a method of treating an endocrine disorder in a patient may include administering to the patient a hybrid gel composition comprising dextran sulfate, at least one polycationic macromolecule, a solvating fluid, embedded endocrine cells, and embedded pluripotent cells. In some embodiments, the hybrid gel compositions described herein may be used to treat endocrine disorders in a patient by, for example, implanting into the patient a composition comprising dextran sulfate (a polyanionic macromolecule), chitosan (a polycationic macromolecule), a buffered solvating fluid, and embedded endocrine cells or endocrine progenitor cells. In certain embodiments, the methods and compositions disclosed herein may be used to treat diabetes expressed either as type I or type II diabetes.

BRIEF DESCRIPTION OF THE FIGURES

FIG. 2A is a scanning electron micrograph of a lyophilized hybrid gel composition according to an embodiment. FIG. 2B is a scanning electron micrograph of a hybrid gel composition showing dextran-$O—SO_3$ deposited on a layer of chitosan. Original magnification for FIGS. 2A and 2B is 1000×.

FIG. 3A-C are histology images of porcine islets embedded in a hybrid gel composition according to an embodiment and maintained in cell culture for 28 days. FIG. 3A is a hematoxylin and eosin (H&E) stain of a low magnification view of a hybrid gel composition containing several viable pancreatic islets as indicated by the arrows (size bar=500 μm). FIG. 3B is an H&E stain of viable pancreatic islets (PIs) surrounded by bright red staining of a hybrid gel composition (size bar=50 μm). FIG. 3C is an islet immunohistochemical stain/hematoxylin stain of the viable PIs in the hybrid gel composition of FIG. 3B (size bar=50 μm).

FIG. 4 is a table of porcine C-peptide assays of cell culture medium from pig islets in conventional plate culture (free pig islets) and islets within a hybrid gel composition (HGC) according to an embodiment. Samples of culture medium from days 1, 2, 5 & 7 (D1-D7) were assayed. Blank control medium was cell culture without exposure to free or embedded porcine islets within a HGC.

DETAILED DESCRIPTION

Figure 1:
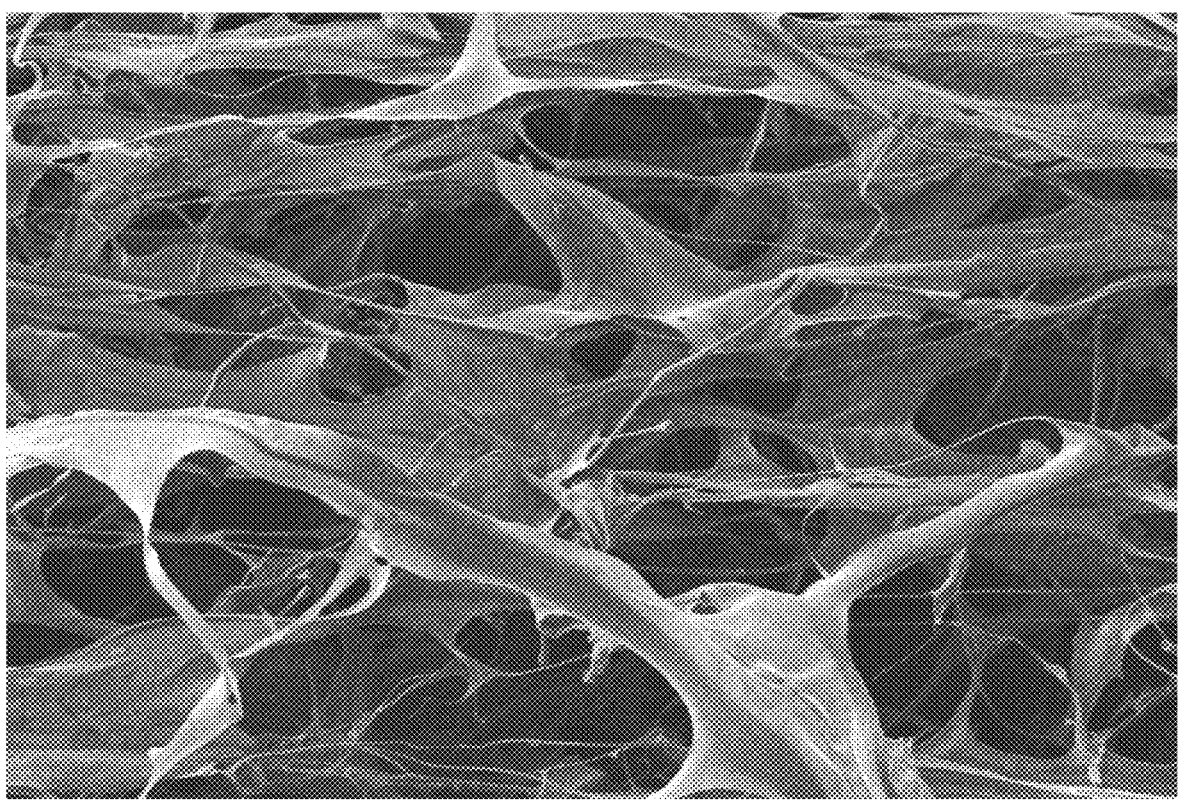
FIG. 1 is a scanning electron micrograph of lyophilized chitosan according to an embodiment of the present invention. Original magnification—100×.

Disclosed herein are compositions and methods of creating hybrid gel compositions. Before the present compositions and methods are described, it is to be understood that this invention is not limited to the particular processes, compositions, or methodologies described, as these may vary. It is also to be understood that the terminology used in the description is for the purpose of describing the particular versions or embodiments only, and is not intended to limit the scope of the present invention which will be limited only by the appended claims. Unless defined otherwise, all technical and scientific terms used herein have the same meanings as commonly understood by one of ordinary skill in the art. Although any methods and materials similar or equivalent to those described herein may be used in the practice or testing of embodiments of the present invention, the preferred methods, devices, and materials are now described. All publications mentioned herein are incorporated by reference in their entirety. Nothing herein is to be construed as an admission that the invention is not entitled to antedate such disclosure by virtue of prior invention.

It must be noted that as used herein, and in the appended claims, the singular forms "a," "an," and "the" include plural reference unless the context clearly dictates otherwise. Thus, for example, reference to a "glycosaminoglycan" is a reference to one or more glycosaminoglycans and equivalents thereof known to those skilled in the art. Unless defined otherwise, all technical and scientific terms used herein have the same meanings as commonly understood by one of ordinary skill in the art. As used herein, the term "comprising" means "including, but not limited to."

As used herein, all claimed numeric terms are to be read as being preceded by the term, "about," which means plus or minus 10% of the numerical value of the number with which it is being used. Therefore, a claim to "50%" means "about 50%" and encompasses the range of 45%-55%.

The term "treating" includes administration of the disclosed compositions thereby to prevent the symptoms, alleviate symptoms, delay the onset of, or eliminate the disease, condition, or disorder.

The term "macromolecule" as used herein includes, but is not limited to, any molecule of large molecular weight or formed by polymerization of smaller molecules, such as polymeric monomers/dimers, etc., proteins, lipids, polysaccharides or nucleic acids.

The term "solvating fluid" as used herein includes, but is not limited to, any fluid that dissolves a solute or solutes. Solvating fluid may also be referred to as a fluid of hydration.

The term "powder" as used herein includes any small particle of a material that does not contain any moisture which would cause the individual small particles to aggregate or form larger associations of the small particles or dissolve.

The term "biocompatible" as used herein refers to a composition being harmonious with life; not having toxic or injurious effects on biological function at molecular, cellular or tissue levels; and is compatible with living tissue. While parameters of biocompatibility may be measured by various means, compositions that do not elicit an immune response (or only a minimal response) are biocompatible. Similarly, compositions that are not toxic to an organism or to juxtaposed cells are biocompatible.

The term "composition" includes those which are generated by polycationic and polyanionic macromolecules. The compositions may include additional components and/or a volume of fluid.

The term "hybrid gel composition" includes hybrid hydrocolloid/hydrogel composition, hydrocolloid composition, hybrid gel, hydrogel, fluid mass hydrocolloid material, hydrogel material, hybrid gel material, hydrated hybrid gel composition, hydrated hybrid gel material, and fully hydrated constructs.

The term "dry blend" encompasses compositions of dry polycationic macromolecules, dry polyanionic macromolecules, and the combination of dry polycationic macromolecules and dry polyanionic macromolecules both of which have low enough moisture contents so as not to have any noticeable clumping or grouping that may prevent uniform distribution of the dry particles among one another. Macromolecules may be mechanically blended together, hand mixed, sifted together, or mixed using any other method known in the art.

The term "anhydrous" refers to a composition, macromolecule, molecule, particle, material, or substance having no water. The term "anhydrous" is used interchangeably herein with "dry".

The term "plurality" encompasses multiple species of polyanionic macromolecules, multiple species of polycationic macromolecules, multiple molecules of a homogeneous species of polyanionic macromolecules, and multiple molecules of a homogeneous species of polycationic macromolecules.

The term "stiffness" refers to a composition's ability to resist deformation in response to an applied force. As used herein, the term "stiffness" describes a composition's elastic modulus and is defined by the ratio of stress (force applied per unit area along an axis) over strain (degree of deformation over initial length along that axis). Stiffness also means tensegrity, tensional integrity, or floating compression.

In some embodiments, a composition may comprise a plurality of polycationic macromolecules and a plurality of polyanionic macromolecules. In some embodiments, the plurality of polycationic macromolecules and the plurality of polyanionic macromolecules are anhydrous. Examples of polyanionic macromolecules include, but are not limited to, dextran sulfate and glycosaminoglycans, such as dermatan sulfate, keratan sulfate, heparan sulfate, and hyaluronan, or a combination thereof. For example, the plurality of polyanionic macromolecules may include dextran sulfate and an additional glycosaminoglycan, such as hyaluronan. In these embodiments, the dextran sulfate may have a low molecular weight of about 5 kilodaltons. The plurality of polycationic macromolecules may include, but are not limited to, cellulose, chitosan, any other linear polysaccharide capable of being protonated, or a combination thereof. For example, the plurality of polycationic macromolecules may include chitosan and cellulose.

In some embodiments, dextran sulfate may be used as the polyanionic macromolecule to engage a polycationic macromolecule in the composition. In some embodiments, the dextran sulfate is anhydrous. In some embodiments, chitosan may be used as the polycationic macromolecule. In such embodiments, dextran sulfate electrostatically interacts with chitosan. Where a second polyanionic macromolecule may be used with a primary polyanionic macromolecule, the second polyanionic macromolecule may be a glycosaminoglycan. In some embodiments, such glycosaminoglycans may include hyaluronan, operating independently as a polyanionic macromolecule or as a companion (polyanionic macromolecule) to dextran sulfate.

Dextran sulfate, a polyanionic macromolecule, provides unique physical and biologic properties that contribute valuable structural and mechanical properties for the composition. Dextran sulfate has a specific molecular morphology providing the molecule with a high level of physical flexibility. Dextran sulfate comprises glucose molecules having three axes of rotation about α-1/6 glycosidic linkages uniformly joining the glucose molecules. Dextran sulfate also has a low persistence length ($L_p$) value of 1.6 nm, indicating low stiffness as well as high flexibility. As a result, dextran sulfate may efficiently associate with polycationic macromolecules as well as with cell surface receptors. For example, when dextran sulfate is reacted with chitosan, polyelectrolytic complexes (PEC) of the two macromolecules form by an electrostatic union of dextran sulfate's $RO-SO_3^-$ groups with $-NH_3^+$ groups of chitosan molecules. These insoluble PEC fibers function as the composition's dispersed phase while providing structural and mechanical competency for its three-dimensional architecture.

Toll-like receptors 4 and 2 (TLR-4 and TLR-2), in conjunction with co-receptors myeloid differentiation 2 (MD-2) and CD14, are cell surface receptors expressed by beta cells of the pancreatic islet. These receptors initiate inflammatory and apoptotic responses upregulated in pancreatic islets as a consequence of isolation from the donor pancreas, subsequent storage in vitro, and ultimate transplantation as an autograft or xenograft tissue. In some embodiments, dextran sulfate electrostatically interacts with lysine and arginine in TLR-4 receptors of islet beta cells, preventing the cells' synthesis and secretion of proinflammatory cytokines and their reaction to autocrine or paracrine generated apoptotic cytokines. Additionally, substituting dextran sulfate for hyaluronan as the polyanionic macromolecule removes the risk of low molecular weight hyaluronan fractions generating proinflammatory signals by various mechanisms including binding to TLR receptors.

Dextran sulfate may be sulfated to any degree of sulfation sufficient to achieve biocompatibility and structural advantages. In some embodiments, the composition may be comprised of dextran sulfate that is sulfated from about 8% to about 22%, about 9% to about 20%, about 10% to about 15%, about 10% to about 13%, or any ranges between any of these values (including endpoints). In other embodiments, the composition may be comprised of dextran sulfate that is sulfated from about 17% to about 22%. The sulfation of dextran sulfate results in varying $RO-SO_3^-$ groups attached to each glycosyl group. For example, where the dextran sulfate is sulfated from about 10% to about 13%, approximately one $RO-SO_3^-$ group is attached to each glycosyl group. In another example, where the dextran sulfate is sulfated from about 17% to about 22%, approximately two $RO-SO_3^-$ groups are attached to each glycosyl group.

In some embodiments, dextran sulfate may have a high molecular weight of about 40 kilodaltons to about 2,000 kilodaltons, about 40 kilodaltons to about 1,000 kilodaltons, about 40 kilodaltons to about 500 kilodaltons, to about 40 kilodaltons to about 200 kilodaltons, and any ranges between any of these values (including endpoints). In yet further embodiments, dextran sulfate may be about 40 kilodaltons.

In other embodiments, dextran sulfate may have a low molecular weight of about 2 kDa to about 40 kDa, about 5 kDa to about 40 kDa, about 4 kDa to about 20 kDa, about 5 kDa to about 10 kDa, and any ranges between any of these values (including endpoints). In some embodiments, low molecular dextran sulfate may be 5 kDa.

In some embodiments, the polycationic macromolecule comprises chitosan. Chitosan offers several advantageous biologic properties in support of cell implantation. Chitosan has inherent antimicrobial properties to prevent growth of gram-negative and gram positive bacteria, as well as fungi. Chitosan has varying effects on the innate immune system based on its degree of deacetylation. At deacetylation levels below 90%, chitosan may activate the innate immune system through ficolins which activate the lectin pathway of the complement system. When deacetylation levels are greater than 90%, circulating ficolins do not recognize chitosan and the complement system and immune systems are not activated. Protonated amine groups of chitosan chelate catabolic Zn(II) moieties of matrix metalloproteases (MMPs) thus inhibiting MMP destructive activities (as, for example, in osteoarthritis). Previous hybrid gel compositions have chitosan at 85-87.5% degrees of deacetylation.

Deacetylation of chitosan may also result in an increase of primary amines, thus changing the pKa of its protonated amine groups, and altering the degree of ionization of protonated amine groups as a function of environmental pH. Chitosan has a pKa of about 6.5. Variation of chitosan's pKa may facilitate the formation process of the composition when fully hydrated and act as a buffering system to maintain environmental pH at acceptable physiologic levels. In some embodiments, the pKa may be decreased due to increased deacetylation of chitosan. In some embodiments, chitosan may be deacetylated to at least 60%, at least 70%, at least 80%, at least 90%, at least 100%, or a range between any of these values. In certain embodiments, chitosan may be deacetylated to at least 90%. In other embodiments, chitosan may be deacetylated to 100%. In such embodiments, chitosan may be protonated to the degree of about 45% to about 100% of available amine groups, about 50% to about 90% of available amine groups, about 60% to about 80% of available amine groups, and any percentage in between any of these values (including endpoints).

In some embodiments, where dry chitosan is used as the polycationic macromolecule, it may be presented as collections of individual fines or particles in the forms of flakes, leaflets, or shards; each comprising area dimensions of up to about 0.2 mm$^2$, about 0.4 mm$^2$, about 0.6 mm$^2$, about 0.8 mm$^2$, about 1.0 mm$^2$, about 1.2 mm$^2$, about 1.4 mm$^2$, about 1.6 mm$^2$, or about 2.0 mm$^2$. In other embodiments, the chitosan flakes, leaflets, or shards may have a thickness dimension of about 0.5 µm to about 15.0 µm, about 1.0 µm to about 14.0 µm, about 2.0 µm to about 12.0 µm, about 4.0 µm to about 10.0 µm, about 6.0 µm to about 8.0 µm, or any ranges between any of these values (including endpoints). FIG. 1 shows a scanning electron micrograph of lyophilized chitosan, with an original magnification of 100×. In some embodiments, the chitosan may be a single polycationic macromolecule. In some embodiments, the chitosan may be presented as a single entity resembling an intact velour whose partitions answer to the definition of thickness stated above.

Mixing of dextran sulfate and polycationic macromolecules may be done at varying charge ratios (n$^+$/n$^-$) to achieve varying functional properties. As such, charge ratios of the polycationic macromolecule (n$^+$)/polyanionic macromolecule (n$^-$) may be about 0.1, about 0.2, about 0.3, about 0.4, about 0.5, about 0.6, about 0.7, about 0.8, about 0.9, about 1.0, about 2.0, about 3.0, about 4.0, about 5.0, about 6.0, about 7.0, about 8.0, and any value between any of these values (including endpoints). In particular embodiments, the charge ratio of the polycationic macromolecule and dextran sulfate may be 5.85. In other embodiments, the charge ratio may be based on a combination of polycationic macromolecules and polyanionic macromolecules. In some embodiments, the n$^-$ charges may dominate over the n$^+$ charges thus reversing the charge ratio of n$^+$/n$^-$ to equal less than 1.0. In further embodiments, the mixing of dextran sulfate and polycationic macromolecules may be done at varying mass ratios. As such, mass ratios of the polycationic macromolecule:polyanionic macromolecule may be about 1:1, about 1:2, about 1:3, about 1:4, about 1:5, about 1:10, about 1:20, about 2:1, about 3:1, about 4:1, about 5:1, about 10:1, about 20:1, and any value between any of these values (including endpoints).

In some embodiments, the composition's dry blend comprised of polyanionic macromolecules and polycationic macromolecules may additionally include one or more biologically active agents. The biologically active agents may include therapeutic pharmaceutical compounds, growth and trophic factors and their analogs, hormones, morphogens, cytotoxic agents, phage vectors, virii vectors, exosomes, artificial chromosomes, antibiotics, antineoplastics, anticoagulants, whole serum constituents, C1-Inh, sCR1, sDAF, sMCP, sMCP-DAF, sCD59, Anti-05, Anti-C3, Anti-C3a, Anti-CSa, C5a mutants, compstatin, RNA aptamer, BCX-1470, FUT-175, K-76, or thioester inhibitors. In particular embodiments, biologically active agents may include Reg-family proteins in general, Reg subfamilies II and III, peptide fragments of Reg-family proteins, peptide fragments of Reg subfamilies II and III, islet neogenesis-associated protein (INGAP), peptide fragments of INGAP, peptides that specifically bind an α5β1 integrin, exendin-4, betacellulin, islet neogenesis-associated protein, islet neogenesis-associated protein fractions, islet neogenesis-associated protein derivatives, or serum albumin.

Additional embodiments may have peptide fragments attached to either a polycation or a polyanion by electrostatic interaction, covalent bonding, and/or hydrogen bonding. Such peptide fragments are synthesized to provide the peptide fragment with specific biologic properties such as enhanced cell attachment and/or induction or inhibition of progenitor cell and stem cell differentiation. In some embodiments, these peptide fragments may be added to the composition's dry blend of polyanionic macromolecules and polycationic macromolecules as additional dry particles.

U.S. Pat. No. 5,834,590 identifies the nucleotide sequence of hamster INGAP and hamster INGAP fragments and is incorporated by reference herein. An example of INGAP may be human insulin neogenesis-associated protein (hINGAP) (Genbank Acc. No. NP_002571; SEQ ID NO: 1). U.S. Pat. No. 7,393,919 identifies human REG3A and human INGAP and U.S. Publication 2011/0171178A1 identifies human proIslet peptides (HIPs), which are active fragments of human REG3A, both are incorporated by reference herein. HIP2 is the active fragment listed in Table 1 as SEQ ID NO: 2, HIP3 is SEQ ID NO: 34, and HIP1 is SEQ ID NO: 35. Additional examples of peptides and proteins of the Reg-family and INGAP family include, but are not limited to, the following:

TABLE 1

| | | | | | | | | | | | | | | |
|---|---|---|---|---|---|---|---|---|---|---|---|---|---|---|
| Human REG3A | I | G | L | H | D | P | T | Q | G | T | E | P | N | G | SEQ ID NO: 2 |
| Chimp REG3A | I | G | L | H | D | P | T | Q | G | S | E | P | D | G | SEQ ID NO: 3 |
| Hamster INGAP | I | G | L | H | D | P | S | H | G | T | L | P | N | G | SEQ ID NO: 4 |
| Mouse REG3A | I | G | L | H | D | P | T | M | G | Q | Q | P | N | G | SEQ ID NO: 5 |
| Norway Rat REG3 | I | W | L | H | D | P | T | M | G | Q | Q | P | N | G | SEQ ID NO: 6 |

TABLE 1-continued

| Name | | | | | | | | | | | | | | SEQ ID |
|---|---|---|---|---|---|---|---|---|---|---|---|---|---|---|
| Cow REG3 | | I | G | L | H | D | P | T | E | G | S | E | P | D | A | SEQ ID NO: 7 |
| Dog REG3 | | M | G | L | H | D | P | T | E | G | Y | E | P | N | A | SEQ ID NO: 8 |
| Sheep REG3 | | I | G | L | H | D | P | T | E | G | S | E | P | N | A | SEQ ID NO: 9 |
| Human REG1A | | I | G | L | H | D | P | K | K | N | R | R | W | H | W | SEQ ID NO: 10 |
| Human REG1B | | I | G | L | H | D | P | K | K | N | R | R | W | H | W | SEQ ID NO: 11 |
| Rat REG1 | | I | G | L | H | D | P | K | N | N | R | R | W | H | W | SEQ ID NO: 12 |
| Mouse REG1 | | T | G | L | H | D | P | K | R | N | R | R | W | H | W | SEQ ID NO: 13 |
| Mouse REG2 | | T | G | L | H | D | P | K | S | N | R | R | W | H | W | SEQ ID NO: 14 |
| Hamster REG2 | | I | G | L | H | D | P | K | N | N | R | R | W | H | W | SEQ ID NO: 15 |
| Rat REG3 | | I | W | L | H | D | P | T | M | G | Q | Q | P | N | G | SEQ ID NO: 16 |
| Rat PAP/REG3B | | I | G | L | H | D | P | T | L | G | G | E | P | N | G | SEQ ID NO: 17 |
| Rat PAP3 | | I | G | L | H | D | P | T | L | G | Q | E | P | N | R | SEQ ID NO: 18 |
| Mouse REG3A | | I | G | L | H | D | P | T | M | G | Q | Q | P | N | G | SEQ ID NO: 19 |
| Mouse REG3B | | I | G | L | H | D | P | T | L | G | A | E | P | N | G | SEQ ID NO: 20 |
| Mouse REG3G | | I | G | L | H | D | P | T | L | G | Y | E | P | N | R | SEQ ID NO: 21 |
| Rat REG3G | | I | G | L | H | D | P | T | L | G | Q | E | P | N | R | SEQ ID NO: 22 |
| Hamster REG3G | | I | G | L | H | D | P | T | L | G | Q | E | P | N | G | SEQ ID NO: 23 |
| Human REG3G | | I | G | L | H | D | P | T | Q | G | S | E | P | D | G | SEQ ID NO: 24 |
| Mouse REG3S | | I | G | L | H | D | L | S | L | G | S | L | P | N | E | SEQ ID NO: 25 |
| Bovine PTP | | I | G | L | H | D | P | T | E | G | S | E | A | N | A | SEQ ID NO: 26 |
| Hamster INGAP | | I | G | L | H | D | P | S | H | G | T | L | P | N | G | SEQ ID NO: 27 |
| Human REG4 | | I | G | L | H | D | P | Q | K | R | Q | Q | W | Q | W | SEQ ID NO: 28 |
| Mouse REG4 | | I | G | L | H | D | P | Q | K | K | Q | L | W | Q | W | SEQ ID NO: 29 |
| Chimp REG4 | | I | G | L | H | D | P | T | Q | G | S | E | P | D | G | SEQ ID NO: 30 |
| Cow REG4 | | I | G | L | H | D | P | T | E | G | S | E | P | D | A | SEQ ID NO: 31 |
| Dog REG4 | | M | G | L | H | D | P | T | E | G | Y | E | P | N | A | SEQ ID NO: 32 |
| Sheep REG4 | | I | G | L | H | D | P | T | E | G | S | E | P | N | A | SEQ ID NO: 33 |
| HIP3 | | I | G | L | H | D | P | T | Q | G | T | E | P | N | G E | SEQ ID NO: 34 |
| HIP1 | W | I | G | L | H | D | P | T | Q | G | T | E | P | N | G | SEQ ID NO: 35 |

In other embodiments, the composition may include a solvating fluid to form a hybrid gel composition. In some embodiments, a composition may comprise at least one polyanionic macromolecule, at least one polycationic macromolecule, and a solvating fluid. In some embodiments, the composition may be a hybrid gel composition. The hybrid gel composition may provide a biocompatible microenvironment and may function as a cell transplantation platform. In some embodiments, a hybrid gel composition may include dextran sulfate, at least one polycationic macromolecule, and a solvating fluid. Such embodiments thereby form a hybrid gel composition possessed of advantageous structural, mechanical, and biologic properties. The polyanionic macromolecules may include all polyanionic macromolecules as described previously. The polycationic macromolecules may include all polycationic macromolecules as described previously. In some embodiments, the polycationic macromolecules may include chitosan and/or cellulose.

Figure 2A:
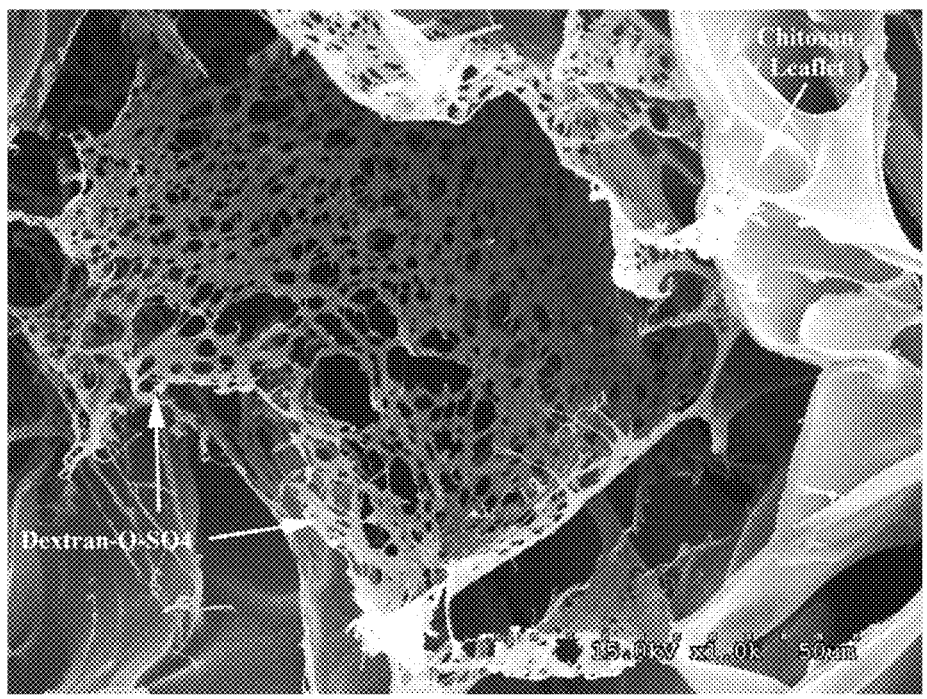
FIG. 2A-B show dry chitosan mixtures ($CT-NH_3^+$) hydrated with a solvating fluid containing dissolved dextran-$O—SO_3^-$ according to an embodiment.
Figure 2B:
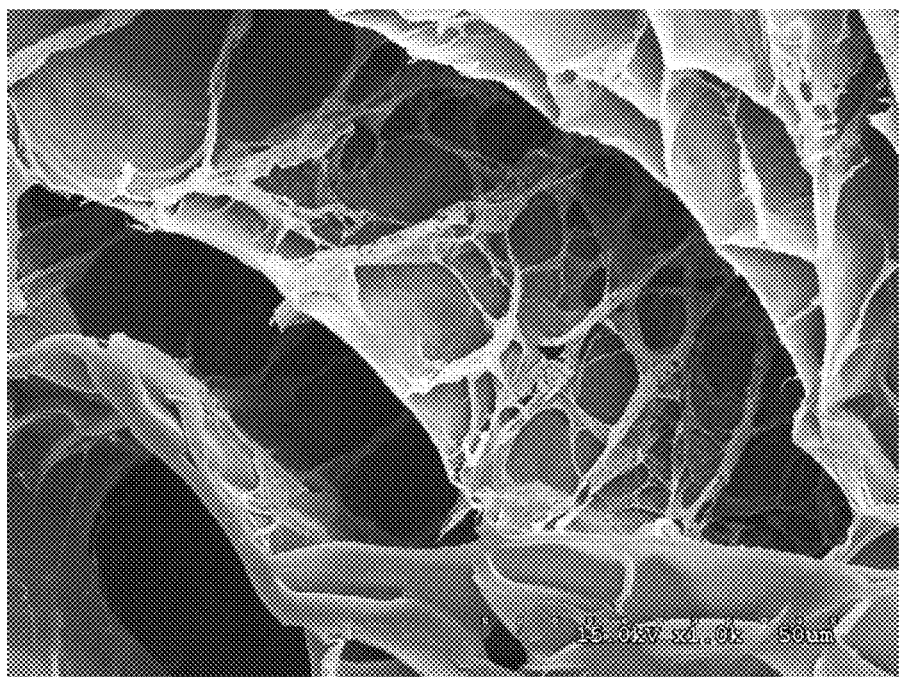

The hybrid gel composition of some embodiments described herein may comprise polyanionic macromolecules selected from glycosaminoglycans such as dermatan sulfate, dextran sulfate, heparan sulfate, hyaluronan, and keratan sulfate or a combination thereof. In some embodiments, dextran sulfate may be used as the polyanionic macromolecule. The dextran sulfate may engage a polycationic macromolecule in the hybrid gel composition. In some embodiments, the dextran sulfate is anhydrous. In some embodiments, chitosan may be used as the polycationic macromolecule. In such embodiments, dextran sulfate electrostatically interacts with chitosan. A scanning electron micrograph of a lyophilized hybrid gel composition of chitosan ($CT-NH_3^+$) and dextran sulfate is shown in FIG. 2A. A scanning electron micrograph of a hybrid gel composition showing dextran sulfate (dextran-$O-SO_3^-$) deposited on a layer of chitosan is shown in FIG. 2B. FIG. 2A-B both have an original magnification of 1000×. In some embodiments, the polycationic macromolecules may be selected from cellulose, chitosan, any other linear polysaccharide capable of being protonated, or a combination thereof. Where a second polyanionic macromolecule may be used with a primary polyanionic macromolecule, the second polyanionic macromolecule may be a glycosaminoglycan. In some embodiments, such glycosaminoglycans may include hyaluronan, operating independently as a polyanionic macromolecule or as a companion (polyanionic macromolecule) to dextran sulfate.

Dextran sulfate, a polyanionic macromolecule, provides unique physical and biologic properties that contribute valuable structural and mechanical properties for the hybrid gel composition. Dextran sulfate has a specific molecular morphology providing the molecule with a high level of physical flexibility. Dextran sulfate comprises glucose molecules having three axes of rotation about α-1/6 glycosidic linkages uniformly joining the glucose molecules. Dextran sulfate also has a low persistence length ($L_p$) value of 1.6 nm, indicating low stiffness as well as high flexibility. As a result, dextran sulfate may efficiently associate with polycationic macromolecules as well as with cell surface receptors. For example, when dextran sulfate is reacted with chitosan, PEC of the two macromolecules form by an electrostatic union of dextran sulfate's $RO-SO_3^-$ groups with $-NH_3^+$ groups of chitosan molecules. These insoluble PEC fibers function as the hybrid gel composition's dispersed phase while providing structural and mechanical competency for its three-dimensional architecture.

Toll-like receptors 4 and 2 (TLR-4 and TLR-2), in conjunction with co-receptors myeloid differentiation 2 (MD-2) and CD14, are cell surface receptors expressed by beta cells of the pancreatic islet. These receptors initiate inflammatory and apoptotic responses upregulated in pancreatic islets as a consequence of isolation from the donor pancreas, subsequent storage in vitro, and ultimate transplantation as an autograft or xenograft tissue. In some embodiments, dextran sulfate electrostatically interacts with lysine and arginine in TLR-4 receptors of islet beta cells, preventing the cells' synthesis and secretion of proinflammatory cytokines and their reaction to autocrine or paracrine generated apoptotic cytokines. Additionally, substituting dextran sulfate for hyaluronan as the polyanionic macromolecule removes the risk of low molecular weight hyaluronan fractions generating proinflammatory signals by various mechanisms including binding to TLR receptors.

Dextran sulfate may be sulfated to any degree of sulfation sufficient to achieve biocompatibility and structural advantages. In some embodiments, the hybrid gel composition may be comprised of dextran sulfate that is sulfated from about 8% to about 22%, about 9% to about 20%, about 10% to about 15%, about 10% to about 13%, or any ranges between any of these values (including endpoints). In other embodiments, the hybrid gel composition may be comprised of dextran sulfate that is sulfated from about 17% to about 22%. The sulfation of dextran sulfate results in varying $RO-SO_3^-$ groups attached to each glycosyl group. For example, where the dextran sulfate is sulfated from about 10% to about 13%, approximately one $RO-SO_3^-$ group is attached to each glycosyl group. In another example, where the dextran sulfate is sulfated from about 17% to about 22%, approximately two $RO-SO_3^-$ groups are attached to each glycosyl group.

In some embodiments, dextran sulfate may have a high molecular weight of about 40 kilodaltons to about 2,000 kilodaltons, about 40 kilodaltons to about 1,000 kilodaltons, about 40 kilodaltons to about 500 kilodaltons, to about 40 kilodaltons to about 200 kilodaltons, and any ranges between any of these values (including endpoints). In yet further embodiments, dextran sulfate may be about 40 kilodaltons. Higher molecular weight dextran sulfate provides increased mechanical and structural properties to the hybrid gel composition through formation of polyelectrolytic complex fibers with high molecular weight chitosan.

In other embodiments, dextran sulfate may have a low molecular weight of about 2 kDa to about 40 kDa, about 5 kDa to about 40 kDa, about 4 kDa to about 20 kDa, about 5 kDa to about 10 kDa, and any ranges between any of these values (including endpoints). In some embodiments, low molecular dextran sulfate may be 5 kDa.

In some embodiments, the polycationic macromolecule may comprise chitosan. Chitosan offers several advantageous biologic properties in support of cell implantation with the hybrid gel composition. Chitosan has inherent antimicrobial properties to prevent growth of gram-negative and gram positive bacteria, as well as fungi. Chitosan has varying effects on the innate immune system based on its degree of deacetylation. At deacetylation levels below 90%, chitosan may activate the innate immune system through ficolins which activate the lectin pathway of the complement system. When deacetylation levels are greater than 90%, circulating ficolins do not recognize chitosan and the complement system and immune systems are not activated. Protonated amine groups of chitosan chelate catabolic Zn(II) moieties of matrix metalloproteases (MMPs) thus inhibiting MMP destructive activities (as, for example, in osteoarthritis). Previous compositions have chitosan at 85-87.5% degrees of deacetylation.

Deacetylation of chitosan may also result in an increase of primary amines, thus changing the pKa of its protonated amine groups, and altering the degree of ionization of protonated amine groups as a function of environmental pH. Chitosan has a pKa of about 6.5. Variation of chitosan's pKa may facilitate the formation process of the hybrid gel composition and act as a buffering system to maintain environmental pH at acceptable physiologic levels. In some embodiments, the pKa may be decreased due to increased deacetylation of chitosan. In some embodiments, chitosan may be deacetylated to at least 60%, at least 70%, at least 80%, at least 90%, at least 100%, or a range between any of these values. In certain embodiments, chitosan may be deacetylated to at least 90%. In other embodiments, chitosan may be deacetylated to 100%. In such embodiments, chitosan may be protonated to the degree of about 45% to about 100% of available amine groups, about 50% to about 90% of available amine groups, about 60% to about 80% of available amine groups, and any percentage in between any of these values (including endpoints).

In some embodiments, where dry chitosan is used as the polycationic macromolecule, it may be presented as collections of individual fines or particles in the forms of flakes, leaflets or shards; each comprising area dimensions of up to about $0.2\ mm^2$, about $0.4\ mm^2$, about $0.6\ mm^2$, about $0.8\ mm^2$, about $1.0\ mm^2$, about $1.2\ mm^2$, about $1.4\ mm^2$, about $1.6\ mm^2$, or about $2.0\ mm^2$. In other embodiments, the chitosan flakes, leaflets, or shards may have a thickness dimension of about 0.5 μm to about 15.0 μm, about 1.0 μm to about 14.0 µm, about 2.0 µm to about 12.0 µm, about 4.0 µm to about 10.0 µm, about 6.0 µm to about 8.0 µm, or any ranges between any of these values (including endpoints). In some embodiments, the chitosan may be a single polycationic macromolecule. In some embodiments, the chitosan may be presented as a single entity resembling an intact velour whose partitions answer to the definition of thickness stated above.

Mixing of dextran sulfate and polycationic macromolecules may be done at varying charge ratios ($n^+/n^-$) to achieve varying functional properties. As such, charge ratios of the polycationic macromolecule ($n^+$)/polyanionic macromolecule ($n^-$) may be about 0.1, about 0.2, about 0.3, about 0.4, about 0.5, about 0.6, about 0.7, about 0.8, about 0.9, about 1.0, about 2.0, about 3.0, about 4.0, about 5.0, about 6.0, about 7.0, about 8.0, and any value between any of these values (including endpoints). In particular embodiments, the charge ratio of the polycationic macromolecule and dextran sulfate may be 5.85. In other embodiments, the charge ratio may be based on a combination of polycationic macromolecules and polyanionic macromolecules. In some embodiments, the $n^-$ charges may dominate over the $n^+$ charges thus reversing the charge ratio of $n^+/n^-$ to equal less than 1.0. In further embodiments, the mixing of dextran sulfate and polycationic macromolecules may be done at varying mass ratios. As such, mass ratios of the polycationic macromolecule:polyanionic macromolecule may be about 1:1, about 1:2, about 1:3, about 1:4, about 1:5, about 1:10, about 1:20, about 2:1, about 3:1, about 4:1, about 5:1, about 10:1, about 20:1, and any value between any of these values (including endpoints).

In other embodiments, the composition resulting from hydration of the polycationic macromolecule and the polyanionic macromolecule in the solvating fluid is, in fact, a hybrid gel composition comprising hydrocolloid and hydrogel fractions intercalated among one another. Hydrocolloid fractions are generated by formation of polyelectrolytic complex fibers, self-assembled by electrostatic union of the polycationic macromolecule with the polyanionic macromolecule. These hydrocolloid formations dominate the construct at lower temperatures, for example, temperatures below 25° C. At higher temperatures, for example, physiologic temperature of 37° C., heat energy induces transfer of protons from the polycationic macromolecule (e.g. chitosan) to the buffer (e.g. glycerol phosphate and/or bicarbonate, provided by the solvating fluid) thereby deionizing the polycationic macromolecule (e.g. chitosan) and allowing attractive intermolecular forces (e.g. hydrogen bonding and van der Waal's forces) to form a thermoreversible hydrogel fraction in regions of unreacted, homogeneous polycationic macromolecules.

In some embodiments, the hybrid gel compositions of embodiments herein may be further described as a fluid mass, bound by a defined, three-dimensional network of thin threads and membranes of insoluble, polyelectrolytic complex interactions of polycationic and polyanionic macromolecules; the dispersed phase of the hydrocolloid fraction. By combining a solvating fluid with a mixture of dry polycationic macromolecules and dry polyanionic macromolecules, these macromolecules may self-assemble via electrostatic bonding of polycationic macromolecules and polyanionic macromolecules, thereby creating insoluble, polyelectrolytic complex (PEC) fibers and membranes. In some embodiments, polycationic macromolecules, polyanionic macromolecules, and the solvating fluid combine to form a three-dimensional hybrid gel composition that may have a network of insoluble, PEC complexes. In some embodiments, PEC fibers of insoluble, polyelectrolytic complexes demonstrate diameters of about 100 nm to about 500 µm, about 500 nm to about 300 µm, about 1 µm to about 100 µm, about 5 µm to about 50 µm, about 10 µm to about 25 µm, and any ranges between any of these values (including endpoints).

In some embodiments, hybrid gel compositions may be hydrated with a solvating fluid. A solvating fluid may include, without limitation, ionizing solvents, for example, water, or any other suitable solvent or combination of solvents. A solvating fluid may be customized, where the levels of acidity, alkalinity, and osmolarity may be adjusted to accommodate the intended in vivo performance of the hybrid gel composition. Where a solute is dissolved in a solvent, the molar concentration may be described by osmolarity. For example, a solvating fluid comprising dissolved macromolecules may have an osmolarity of about 100 mOsmol/L to about 800 mOsmol/L, about 200 mOsmol/L to about 600 mOsmol/L, about 300 mOsmol/L to about 500 mOsmol/L, and any ranges between any of these values (including endpoints). For example, a solvating fluid may have an osmolarity similar to mammalian cells of about 243 mOsmol/L to about 300 mOsmol/L when the hybrid gel composition will be used either as a three-dimensional cell culture microenvironment or a cell transplantation platform. In particular embodiments, the solvating fluid may be a water-based solution specifically formulated according to the intended application of the hybrid gel composition. Solvating fluids may also have a viscosity slightly greater than that of water to be approximately the same as cell culture media or interstitial fluid when the hybrid gel composition will be used for a three-dimensional cell culture microenvironment. In a particular embodiment of the hybrid gel composition where pancreatic islet cells, or endocrine progenitor cells in conjunction with mesenchymal stem cells are embedded, a solvating fluid may have an osmolarity of about 255 mOsmol/L to about 295 mOsmol/L and a viscosity approximately the same as cell culture media or interstitial fluid. In other embodiments, the solvating fluid may have an osmolarity of about 255 mOsmol/L to about 300 mOsmol/L.

In some embodiments, the solvating fluid may provide water for hydration of dry polyanionic and/or polycationic macromolecules. In other embodiments, the solvating fluid may function as a suspension fluid for cells to be embedded within the hybrid gel composition. In further embodiments, the solvating fluid may provide water for hydration of anhydrous polyanionic and/or polycationic macromolecules and function as a suspension fluid for cells to be embedded within the hybrid gel composition.

In some embodiments, the solvating fluid further comprises dissolved polyanionic macromolecules. Polyanionic macromolecules may be fully dissolved in the solvating fluid prior to hydration of the dry polycationic macromolecules. In other embodiments, the solvating fluid further comprises dissolved low molecular weight dextran sulfate. In some embodiments, the low molecular weight dextran sulfate may be about 2 kDa to about 40 kDa, about 5 kDa to about 40 kDa, about 3 kDa to about 30 kDa, about 4 kDa to about 20 kDa, about 5 kDa to about 10 kDa, and any ranges between any of these values (including endpoints). In some embodiments, low molecular dextran sulfate may be 5 kDa. Low molecular weight dextran may be dissolved into solvating fluids prior to hydration of a dry constituent blend.

In certain embodiments the solvating fluid may be buffered to maintain a target pH level for an implant and its ionic strength may be modulated within the physiologic range of osmolarity (243-300 mOsmoles/L). In some embodiments, the solvating fluid may have an osmolarity of about 255 mOsmol/L, about 265 mOsmol/L, about 275 mOsmol/L, about 285 mOsmol/L, about 295 mOsmol/L, about 300 mOsmol/L, or any range between any of these values (including endpoints). In some embodiments, the solvating fluid may contain at least one polyanionic macromolecule, ½ normal saline, and a buffer. In some embodiments, the buffer may be glycerol phosphate, bicarbonate or a combination thereof.

Solvating fluids may be added dropwise, poured in gradually, or added all at once. In some embodiments, solvating fluids may be added in an amount of about 1 µl/mg of dry blended particles to about 30 µl/mg of dry blended particles, about 5 µl/mg of dry blended particles to about 20 µl/mg of dry blended particles, about 10 µl/mg of dry blended particles to about 15 µl/mg of dry blended particles, or any range between any of these values (including endpoints).

In some embodiments, the disclosed hybrid gel compositions may have regions of unreacted polycationic macromolecules and regions of unreacted polyanionic macromolecules. In some embodiments, a method for forming a hybrid gel composition may include combining anhydrous dextran sulfate and an anhydrous polycationic macromolecule, wherein a dry mixture may be created, and hydrating this dry mixture with a solvating fluid, wherein a network of insoluble, polyelectrolytic complex structures that surround and penetrate regions of unreacted, homogeneous, dextran sulfate and other regions of unreacted, homogeneous polycationic macromolecules may be formed. In other embodiments, the hybrid gel composition may include dextran sulfate, at least one polycationic macromolecule, and solvating fluid to form a three-dimensional hybrid gel composition comprising a network of insoluble, polyelectrolytic complexes. The network of insoluble, polyelectrolytic complex structures may have regions of unreacted dextran sulfate and regions of unreacted polycationic macromolecules. Such regions may be formed from high viscosity gel-sol material being surrounded and penetrated by three-dimensional networks of insoluble, PEC complexes. In some embodiments, these regions may form about 1%, about 5%, about 10%, about 15%, about 20%, about 25%, about 30%, or about 35% of the hybrid gel composition (by volume), or a range between any two of these values (including endpoints). In some embodiments, regions of unreacted polyanionic macromolecules may include unreacted dextran sulfate. In further embodiments, regions of homogeneous chitosan remain unreacted and isolated from the polyanionic macromolecules and may result in formation of a thermosensitive, reversible hybrid gel composition.

Additional embodiments may include a cell suspension solution. In some embodiments, the hybrid gel composition may include embedded endocrine cells and embedded pluripotent cells. In some embodiments, the solvating fluid further comprises a cell suspension solution. In other embodiments, the following groups of cells may be suspended in the solvating fluid as homogeneous cell populations or in combinations of cell populations: metabolically mature cells such as adrenal cells, thyroid cells, parathyroid cells, parafollicular cells, pinealocytes, pituitary cells, neurosecretory cells, endocrine progenitor cells, pancreatic islet cells, pluripotent stem cells such as embryonic stem cells (ESC), mesenchymal stem cells (MSC), induced pluripotent stem cells (iPSCs), or combinations thereof. In particular embodiments, cells suspended in the solvating fluid may comprise endocrine progenitor cells. In some embodiments, the embedded endocrine cells and embedded pluripotent cells are suspended in the solvating fluid. A solvating fluid comprised of low molecular weight dextran protects pancreatic islets from attack by the innate immune system of the host organism.

In some embodiments, cells embedded in the hybrid gel composition may be suspended within a solvating fluid and may comprise about 100,000 cells/mL to about 60,000,000 cells/mL, about 200,000 cells/mL to about 50,000,000 cells/mL, about 300,000 cells/mL to about 40,000,000 cells/mL, about 400,000 cells/mL to about 30,000,000 cells/mL, about 500,000 cells/mL to about 20,000,000 cells/mL, about 500,000 cells/mL to about 10,000,000 cells/mL, about 750,000 cells/mL to about 5,000,000 cells/mL, about 1,000,000 cells/mL to about 2,500,000 cells/mL, and any range between any of these values (including endpoints). Subsequently, the solvating fluid, thus charged with cells, may be used to hydrate constituent particles of the dry blend. Upon hydration of the dry constituent molecules with the cell-charged solvating fluid/cell suspension fluid, a hybrid gel composition may be created in which a three-dimensional network of insoluble, polyelectrolytic complex, fibers, and membranes self-assemble to encompass the cells and retain them within the hybrid gel composition's boundaries. In some embodiments, the cells may be stem cells. The cells may be of any phenotype including, for example, embryonic, mesenchymal or iPSCs and their differentiated progeny, endocrine progenitor cells and/or fully differentiated and metabolically active endocrine cells such as pancreatic islets of Langerhans or islet-like cells transdifferentiated from endocrine progenitor cells. The pancreatic islet cells may be used as an autograft, allograft, or xenograft.

In certain embodiments, mesenchymal stem cells (MSCs) may be embedded into the disclosed hybrid gel compositions. MSCs are adult, pluripotent cells capable of differentiating to any of the specific types of connective tissue cells such as adipocytes, osteoblasts, chondrocytes, fibroblasts, and myocytes. MSCs are found in bone marrow, but may have been isolated from other tissues such as adipose tissue. Phenotype selection for MSCs is directed by soluble signaling proteins as well as by information derived from their microenvironments. Addition of MSCs may improve biocompatibility for companion islet cells by creating an immunoprotective environment. Immunoprotection along with a microenvironment comprised of specific biochemical and mechanical properties aid in propagation of particular cell phenotypes resulting in an effective therapeutic composition useful for treatment of numerous disorders as disclosed herein.

The described hybrid gel compositions of embodiments herein, embedded with cells, provide several structural and biologic benefits over previous three-dimensional microenvironments. In some embodiments comprised of dextran sulfate as the polyanionic macromolecule, controlling its degree of sulfation and, therefore, its negative charge density, allows customization of dextran sulfate in a dry blend and in solvating fluids. Negative charge density of the polyanionic macromolecule may be modified by substituting dextran sulfate for the hyaluronan that was used in previous three-dimensional microenvironments. Degrees of sulfation for dextran sulfate may be varied over a wide range to achieve particular degrees of stiffness and interaction with TLR cell surface receptors. In some embodiments where a hybrid gel composition may be comprised of dextran sulfate and chitosan, hydration characteristics of dextran sulfate are much faster than chitosan, resulting in a specific order of addition when solvating fluids are introduced to the dry polycationic macromolecule or the dry blend of polycationic and polyanionic macromolecular particles. Further, dextran sulfate's high negative charge density makes dextran sulfate readily soluble in water in the pH range of 6.4-7.2.

Similarly, incorporation of low molecular weight dextran sulfate in the hybrid gel composition for mesenchymal stem cells (MSCs) or any other cells provides a measure of protection against hypoxia-induced apoptosis during transfer of cells into the hybrid gel composition and incorporation into host tissue. The hybrid gel composition embedded with cells may be inserted into a sterile cell culture supplied with an excess of cell culture media or injected via needle or catheter for transplantation of its cell cargo into host tissue.

In some embodiments, a hybrid gel composition may include dextran sulfate, chitosan, a solvating fluid, and embedded porcine islet cells. FIG. 3A-C are histology images of porcine islets embedded on the hybrid gel composition. The hybrid gel composition in FIG. 3A-C were maintained in cell culture for 28 days. An H&E stain of a low magnification of the hybrid gel composition showed several viable pancreatic islets as shown in FIG. 3A by the arrows (size bar=500 μm). An H&E stain of viable PIs surrounded by bright red staining of the hybrid gel composition is shown in FIG. 3B (size bar=50 μm). An immunohistochemical stain and hematoxylin stain of the viable PIs in the hybrid gel composition is shown in FIG. 3C (size bar=50 μm). A table of porcine C-peptide assays of cell culture medium from pig islets in conventional plate culture (free pig islets) and islets within the hybrid gel composition (HGC) is shown in FIG. 4. A C-peptide analysis for cultures of porcine islets may indicate islet cell viability. There was a progressive decline of C-peptide concentration in cell culture medium from day 1 to day 7 for pig islets in the HGC, but continued measurable C-peptide confirms the presence of viable islets at all time points for free pig islets and islets within the HGC.

In some embodiments, the solvating fluid may contain at least one dissolved polyanionic macromolecule, ½ normal saline, and a buffer. The buffer may be glycerol phosphate. The embedded endocrine cells and the embedded pluripotent cells may be suspended in the solvating fluid. The embedded endocrine cells and the embedded pluripotent cells may be pancreatic islet cells, adrenal cells, thyroid cells, parathyroid cells, parafollicular cells, pinealocytes, pituitary cells, mesenchymal stem cells, neurosecretory cells, endocrine progenitor cells, iPSCs, or a combination thereof. The embedded endocrine cells and the embedded pluripotent cells may be stem cells.

In some embodiments, the stiffness of the hybrid gel composition may be controlled by the solvating fluid. In other embodiments, the low molecular weight dextran sulfate in the solvating fluid may be used to control the stiffness of the hybrid gel composition. The stiffness may be measured by Young's modulus using any instrument known in the art. The stiffness of the hybrid gel composition influences the cellular response of the embedded cells. Different amounts of stiffness cause different cellular responses. The embedded cells retain mechanical information from the surrounding environment which can influence the embedded cells phenotype. A stiffness of about 0.25 kiloPascals (kPa) to about 1 kPa of the hybrid gel composition promotes neurogenesis. A stiffness of about 10 kPa of the surrounding environment from the hybrid gel composition promotes myogenesis. A stiffness of about 20 kPa of the hybrid gel composition promotes cartilage cell differentiation. A stiffness of about 30 kPa to about 50 kPa of the hybrid gel composition promotes osteogenesis. In some embodiments, the stiffness of the hybrid gel composition may be about 0.5 kPa to about 60 kPa. In some embodiments, the stiffness of the hybrid gel composition may be about 0.25 kPa, about 0.5 kPa, about 0.75 kPa, about 1 kPa, about 2 kPa, about 3 kPa, about 5 kPa, about 10 kPa, about 15 kPa, about 20 kPa, about 25 kPa, about 30 kPa, about 35 kPa, about 40 kPa, about 45 kPa, about 50 kPa, about 55 kPa, about 60 kPa, about 70 kPa, about 80 kPa, about 90 kPa, about 100 kPa, or a range between any of these values.

Additional components may be added to the solvating fluid to promote cell viability and growth or direct pluripotent cell differentiation toward a particular phenotype. These additional components may include, for example, autologous and non-autologous serum and serum components, such as fetal bovine serum, albumin, growth factors, morphogens, hormones, cytokines, vitamins, and amino acids, et alia; as well as tissue specific growth factors; morphogens; dextran sulfate, such as, high molecular weight dextran sulfate and low molecular weight dextran sulfate; glycerol phosphate; normal saline; peptides that specifically bind an $\alpha 5\beta 1$ integrin, and products of the regenerating (Reg) gene super-family such as the islet neogenesis-associated growth protein (INGAP; reg). Furthermore, in some embodiments, the solvating fluid may have autologous interstitial fluid. In some embodiments, the solvating fluid may contain extracellular matrix glycoproteins and proteoglycans.

Exemplary structural advantages described herein may improve biocompatibility of the hybrid gel composition for cell therapy. For example, without being bound by theory, the low molecular weight dextran sulfate may interact with the polycationic macromolecule and with toll-like receptors (TLR) of embedded cells in addition to functioning as a PEC crosslinker forming an integral structural component of the fully hydrated and cell-charged hybrid gel composition. Additionally, low molecular weight dextran sulfate has several biologic effects favorable for cell transplantation materials. Low molecular weight dextran sulfate protects cells from recognition by the host complement system by potentiating the C1 complement inhibitor enzyme and inactivating C3 convertase. Potentiation of C1 complement inhibitor enzyme also elicits anticoagulant effects. Binding of low molecular weight dextran sulfate to toll-like receptors may protect cells from recognition and subsequent damage by host organism's innate and acquired immune systems as well as from damaging effects of autocrine and paracrine apoptotic cytokines.

In some embodiments, the hybrid gel composition may additionally include one or more biologically active agents. The biologically active agents may include therapeutic pharmaceutical compounds, growth and trophic factors and their analogs, hormones, morphogens, cytotoxic agents, phage vectors, virii vectors, exosomes, artificial chromosomes, antibiotics, antineoplastics, anticoagulants, whole serum constituents, C1-Inh, sCR1, sDAF, sMCP, sMCP-DAF, sCD59, Anti-05, Anti-C3, Anti-C3a, Anti-CSa, C5a mutants, compstatin, RNA aptamer, BCX-1470, FUT-175, K-76, or thioester inhibitors. In particular embodiments, biologically active agents may include Reg-family proteins in general, Reg subfamilies II and III, peptide fragments of Reg-family proteins, peptide fragments of Reg subfamilies II and III, islet neogenesis-associated protein (INGAP), peptide fragments of INGAP, peptides that specifically bind an $\alpha 5\beta 1$ integrin, exendin-4, betacellulin, islet neogenesis-associated protein, islet neogenesis-associated protein fractions, islet neogenesis-associated protein derivatives, serum albumin, and any combination thereof. Yet other embodiments the biologically active agent may be biologically active peptides, extracellular matrix glycoproteins (e.g. laminin, fibronectin, osteonectin), proteoglycans (e.g. aggrecan, chondroitin sulfate proteoglycan 2, neurocan), additional glycosaminoglycans (e.g. chondroitin sulfate, dermatan sulfate, heparan sulfate, and keratan sulfate), and any combination thereof. In some embodiments, such agents are added to the composition's dry blend of polyanionic and polycationic macromolecules as additional dry particles. In other embodiments, these agents may be dissolved in the solvating fluid and included within the hybrid gel composition.

Additional embodiments may have peptide fragments attached to either a polycationic macromolecule or a polyanionic macromolecule by electrostatic interaction, covalent bonding, and/or hydrogen bonding. In some embodiments, the hybrid gel compositions may have peptide fragments covalently bonded to dextran sulfate. In other embodiments, the hybrid gel compositions may have peptide fragments covalently bonded to hyaluronan. In further embodiments, the hybrid gel compositions may have peptide fragments covalently bonded to at least one polycationic macromolecule. Such peptide fragments are synthesized to provide the peptide fragment with specific biologic properties such as enhanced cell attachment and/or induction or inhibition of progenitor cell and stem cell differentiation. In some embodiments, these peptide fragments may be added as constituents of the hybrid gel composition in the solvating fluid. In other embodiments, these peptide fragments may be added to the composition's dry blend of polyanionic macromolecules and polycationic macromolecules.

As previously described, U.S. Pat. No. 5,834,590 identifies the nucleotide sequence of hamster INGAP and hamster INGAP fragments. An example of INGAP may be human insulin neogenesis-associated protein (hINGAP) (Genbank Acc. No. NP_002571; SEQ ID NO: 1). U.S. Pat. No. 7,393,919 identifies human REG3A and human INGAP and U.S. Publication 2011/0171178A1 identifies human proIslet peptides (HIPs), which are active fragments of human REG3A. HIP2 is the active fragment listed in Table 1 as SEQ ID NO: 2, HIP3 is SEQ ID NO: 34, and HIP1 is SEQ ID NO: 35. Additional examples of peptides and proteins of the Reg-family and INGAP family include, but are not limited to, the peptides and proteins previously stated in Table 1.

Introduction of constituent materials to one another may be in any order or may require a specific order of introduction when addressing different requirements for the composition and/or hybrid gel composition. For example, polyanionic macromolecules and polycationic macromolecules may be combined as dry particles, followed by addition of solvating fluids to the dry blend. Where cells are to be embedded into the hybrid gel composition, cells may be added to a dry blend of polycationic macromolecules and polyanionic macromolecules by suspension in the solvating fluid prior to its application to the dry blend. Alternatively, the polyanionic macromolecules may be initially separated from the polycationic macromolecules by being dissolved in the solvating fluid. In further embodiments, the polyanionic macromolecules dissolved in the solvating fluid may also include cells to be embedded in the hybrid gel composition. In some embodiments, endocrine cells may be added to the hybrid gel composition. In some embodiments, pluripotent cells may be added to the hybrid gel composition. In other embodiments, endocrine cells and pluripotent cells may be added to the hybrid gel composition. Addition of multiple polyanionic macromolecular species may be staged by presenting one species fully dissolved in the solvating fluid while different species of polyanionic macromolecules reside as discrete particles in the dry blend of constituents.

In some embodiments the hybrid gel composition may be comprised of high molecular weight dextran sulfate and chitosan and a solvating fluid, wherein the solvating fluid may additionally include low molecular weight dextran sulfate. In some embodiments, low molecular weight dextran sulfate may be first in the order of reactants since it may be fully dissolved in a solvating fluid before the other polyanionic macromolecules and polycationic macromolecules are introduced to the composition. In other embodiments, high molecular weight dextran sulfate may be next in order of addition because high molecular weight dextran sulfate readily dissolves in a solvating fluid, and chitosan may be the last in the order of addition due to chitosan's relatively slow rate of entering the solvating fluid.

In some embodiments, the polyanionic macromolecules and the polycationic macromolecules are anhydrous and dry blended together, followed by hydration with a solvating fluid. In other embodiments, polyanionic macromolecules are fully dissolved in the solvating fluid while the polycationic macromolecule remains as a dry component until exposed to the solvating fluid. In such an embodiment, solvating fluids may be additionally comprised of a cell suspension solution containing cells to be embedded within the hybrid gel composition. In some embodiments, dextran sulfate may be the polyanionic macromolecule and may not be dry mixed with polycationic macromolecules, but instead added to solvating fluids comprised of a cell suspension solution with cells and low molecular weight dextran sulfate. Polycationic macromolecules may then be the only component in the dry fraction of the composition. When the dry polycationic macromolecule fraction of the composition is exposed to the solvating fluid, further comprised of high molecular weight dextran sulfate, low molecular weight dextran sulfate, and cells; a fully hydrated composition may be generated as a hybrid gel composition including a plurality of cells.

In some embodiments, the hybrid gel compositions described herein may be used as a three-dimensional microenvironment for the delivery of cells, drugs, or therapeutics to a patient to treat a disorder. Cell therapy treatment with the use of the disclosed hybrid gel composition provides a unique delivery method for patients suffering from a variety of diseases and injuries such as, but not limited to, spinal injuries, cartilage damage, bone fractures, wound repair, cardiac therapy, diabetes, liver disease, thyroid disease, pancreatic disease, et alia. In some embodiments, the disorder may be an endocrine disorder such as adrenal disorder, diabetes, glucose homeostasis disorder, thyroid gland disorder, calcium homeostasis disorder, pituitary gland disorder, pineal gland disorder, sex hormone disorder, and any combination thereof. In other embodiments, the patient may have diabetes mellitus, such as type I diabetes mellitus or type II diabetes mellitus. In further embodiments, a method of treating an endocrine disorder in a patient may comprise implanting into the patient a hybrid gel composition including dextran sulfate, at least one polycationic macromolecule, a solvating fluid, embedded endocrine cells, and embedded pluripotent cells. In other embodiments, the hybrid gel compositions may be used for delivery of therapeutic agents. For example, the patient may have cancer, and the hybrid gel composition may deliver anti-cancer, cytotoxic drugs to a targeted area of the body.

In some embodiments, the solvating fluid may contain at least one dissolved polyanionic macromolecule, ½ normal saline, and a buffer. The buffer may be glycerol phosphate. The embedded endocrine cells and the embedded pluripotent cells may be suspended in the solvating fluid. The embedded endocrine cells and the embedded pluripotent cells may be pancreatic islet cells, adrenal cells, thyroid cells, parathyroid cells, parafollicular cells, pinealocytes, pituitary cells, mesenchymal stem cells, neurosecretory cells, endocrine progenitor cells, iPSCs, or a combination thereof. The embedded endocrine cells and the embedded pluripotent cells may be stem cells.

Treatment of endocrine disorders by some embodiments represent an example of the therapeutic application of the hybrid gel composition. Type I diabetes may be an endocrine disorder whose treatment may benefit from improved cell transplantation and engraftment compositions composed of, for example, without limitation, pancreatic islets, and/or endocrine progenitor cells, as homogeneous cell populations or in combination with MSCs, ESCs iPCs. Current treatment modalities for these cells do not provide microenvironments for the transplanted cells and do not offer the transplanted cells protection form immune responses initiated by the innate and acquired immune systems of the host organism. In some embodiments, a hybrid gel composition of high molecular weight dextran sulfate, low molecular weight dextran sulfate, chitosan, and a solvating fluid may be embedded with pancreatic islets of Langerhans alone, or in combination with pluripotent cells identified above, and implanted into a patient to provide treatment for type I diabetes.

Compositions described herein may be administered to the patient by any suitable means such as, without limitation, surgical implantation, intracavitary or subcutaneous injection, injection into organ parenchyma, intramuscular administration, or any combination thereof. The route of administration depends on the disease to be treated and the structure of the compositions. In some embodiments, a hybrid gel composition embedded with cells may be used in vivo by being implanted or injected into a host tissue. As such, hybrid gel compositions may be implanted by any means known in the art, for example, implants may be placed at any surgical site, such as beneath the renal capsule, or within the epididymal fat pad, or as a intrahepatic injection, intraperitoneal implantation, or at any other suitable anatomic site using an appropriate method. In further embodiments, the hybrid gel composition may be used in vivo as a delivery vehicle for drugs, growth factors, morphogens, or any other biologically active agent.

Thus, since the invention disclosed herein may be embodied in other specific forms without departing from the spirit or general characteristics thereof, some of which forms have been indicated, the embodiments described herein are to be considered in all respects illustrative and not restrictive. The scope of the invention is to be indicated by the appended claims, rather than by the foregoing description, and all changes which come within the meaning and range of equivalency of the claims are intended to be embraced therein.

EXAMPLES

Example 1: Hybrid Gel Compositions

Dry preparation of dextran sulfate will result in thin individual flakes. The dry preparation of chitosan will be freeze-dried from a dilute solution and mechanically reduced to thin, individual leaflets. A dry blend of these polyanionic and polycationic macromolecules will be prepared by mixing dry dextran sulfate with dry chitosan.

Example 2: Incorporation and In Vitro Culture of Cells in Hydrated Hybrid Gel Composition The first hybrid gel composition (HC1) will be a dry mixture of high molecular weight dextran sulfate (MW: 40 kDa), hyaluronan, and chitosan at a ratio of 2:1:1, respectively. The second hybrid gel composition (HC2) will be a dry mixture of high molecular weight dextran sulfate (MW: 40 kDa) and chitosan, and will be prepared as a dry mixture at a ratio of 2:1, respectively. The third hybrid gel composition (HC3) will be a dry mixture of hyaluronan and chitosan, and will be prepared as a dry mixture at a ratio of 1:1, respectively. A solvating fluid composed of ½ normal saline, high molecular weight dextran sulfate (MW: 40 kDa) and a buffer suitable for maintaining a solution pH=6.7 (or greater) will be used for suspension of $10 \times 10^6$ hMSCs/mL, 40,000 porcine islet equivalents (IEQ)/mL and low molecular weight dextran sulfate (MW: 5 kDa) sufficient to achieve targeted mechanical properties. The compositions will be mixed vigorously by vortex with the solvating fluid/cell suspension solution to generate a hybrid gel composition containing embedded cells. Two additional solvating fluids with different cell compositions will be prepared, one without MSCs but with human islets and islets of other species and one with MSCs but without human/non-human islet equivalents. These solvating fluids will be prepared separately with each hybrid gel composition and in the same method described above, resulting in nine different groups of hybrid gel compositions (HC1+MSC+Islet, HC1+Islet only, HC1+MSC only, HC2+MSC+Islet, HC2+Islet only, HC2+MSC only, HC3+MSC+Islet, HC3+Islet only, HC3+MSC only), each group prepared in triplicate. The hybrid gel compositions will be placed in 6-well plates containing CMRL medium or other culture medium suitable for maintenance of islet viability and function and kept in a 37° C. incubator with 5% $CO_2$. All hybrid gel compositions will be harvested on days 1, 2, 4, and 6 and culture medium collected and frozen at −80° C. for later analysis of C-peptide content. The harvested hybrid gel compositions will be fixed in 10% neutral buffered formalin and processed for routine paraffin embedding and H&E and insulin immunohistochemical stains. Samples containing MSCs only will serve as negative controls and will be expected to have negative immunohistochemical (IHC) staining for insulin and negative C-peptide levels in the culture medium. Insulin IHC staining in >50% of islet cells will indicate a normal complement of islet β-cells. Sections immunohistochemically stained for insulin will be assessed morphometrically for insulin area fraction using images captured with the Aperio system. Area fractions of each group will be used to assess and compare the relative survival of functional β-cells in each preparation to determine the most optimal formulation. Additionally, C-peptide levels in each group will be compared to assess normal insulin secretion and to compare function of islets in each preparation.

Example 3: In Vivo Testing of Embedded Hydrated Polymer Composition for Islet and Progenitor Cell Transplantation The first hybrid gel composition (HC1) will be a dry mixture of high molecular weight dextran sulfate (MW: 40 kDa), hyaluronan, and chitosan at a ratio of 2:1:1, respectively. The second hybrid gel composition (HC2) will be a dry mixture of high molecular weight dextran sulfate (MW: 40 kDa) and chitosan, and will be prepared as a dry mixture at a ratio of 2:1, respectively. The third hybrid gel composition (HC3) will be a dry mixture of hyaluronan and chitosan, and will be prepared as a dry mixture at a ratio of 1:1, respectively. A solvating fluid composed of ½ normal saline, high Mw dextran sulfate (MW: 40 kDa) and an buffer suitable for maintaining a solution pH=6.7 will be used for suspension of $10\times10^6$ hMSCs/mL, 40,000 porcine islet equivalents (IEQ)/mL, and low molecular weight dextran sulfate (MW: 5 kDa) sufficient to achieve targeted mechanical properties. An additional solvating fluid as described above, but with porcine islet equivalents and no MSCs will be prepared. Each composition will be mixed vigorously by vortex with each solvating fluid, separately, to generate hybrid gel compositions. These hybrid gel compositions will be implanted in mice. Non-diabetic nu/nu mice will be used to avoid confounding factors secondary to diabetes induction and associated metabolic abnormalities, and to avoid the need for immunosuppressive therapy. A total of ten groups of mice will be studied: 1) HC1 only, 2) HC1 with 50 µl of solvating fluid with 2000 porcine islet equivalents, 3) HC1 with 50 µl of solvating fluid with 2000 porcine islet equivalents and $1\times10^6$ mouse MSC, 4) HC2 only, 5) HC2 with 50 µl of solvating fluid with 2000 porcine islet equivalents, 6) HC2 with 50 µl of solvating fluid with 2000 porcine islet equivalents and $1\times10^6$ mouse MSC, 7) HC3 only, 8) HC2 with 50 µl of solvating fluid with 2000 porcine islet equivalents, 9) HC3 with 50 µl of solvating fluid with 2000 porcine islet equivalents and $1\times10^6$ mouse MSC and 10) control group with 2000 porcine islet equivalents and no hydrated polymer. Each group will consist of 15 mice, with 3 mice per day sacrificed on days 3, 7, 14, 21, and 28 post-implantation. Each mouse will be implanted with a hybrid gel composition at 2 sites including the renal subcapsular site and epididymal fat pad.

At sacrifice each implantation site will be separately collected and formalin fixed for 12 hours. Tissues will be processed for routine histology and stained with hematoxylin and eosin stain. Implantation sites will be evaluated by histopathology and semi-quantitatively scored (absent, minimal, mild, moderate, marked) for inflammatory cell infiltrates, neovascularization, fibrosis, and, in implants with cells, for quantity of viable cells. In addition, the width of the inflammatory/fibrosis zone surrounding the implantation sites will be measured morphometrically in the same sections. Sections containing islets or islet progenitor cells will be immunohistochemically stained with insulin and cleaved caspase-3 (apoptosis marker) to assess islet integrity and survival and cell death respectively. Images of these preparations will be captured with the Aperio system and area fractions of insulin (staining area/total area of construct) and cleaved caspase-3 (staining area/total islet area) measured. Neovascularization will also be assessed by von Willibrand factor immunohistochemistry on implants. Reactions to the implantation sites and survival estimates will also be compared to identically evaluated porcine islet xenotransplants from group 4. To assess function of porcine islet xenotransplantants, porcine C-peptide will be measured in blood samples collected at the time of euthanasia from each mouse. Success of islet engraftment will be confirmed by detection of porcine (or human) C-peptide in mouse serum collected at sacrifice, by evidence of viable islets (positive insulin and negative cleaved caspase-1 immunohistochemistry), and survival of greater than 50% of transplanted islets at the 28 day time point. Additional positive indicators will include evidence of neovascularization of transplanted islets and minimal to mild-inflammation and fibrosis at the transplantation site.

What is claimed is:

1. A method for forming a three-dimensional hybrid gel composition comprising:
   combining dextran sulfate and a solvating fluid to form a composition;
   adding at least one polycationic macromolecule to the composition to form the three-dimensional hybrid gel composition, which comprises a network of insoluble, polyelectrolytic complex structures having regions of unreacted polycationic macromolecules; and
   suspending in the solvating fluid cells selected from the group consisting of endocrine cells and pluripotent cells.

2. The method of claim 1, wherein the endocrine cells are selected from the group consisting of pancreatic islet cells, adrenal cells, thyroid cells, parathyroid cells, parafollicular cells, pinealocytes, pituitary cells, neurosecretory cells, and any combination thereof.

3. The method of claim 1, further comprising adding hyaluronan.

4. The method of claim 3, further comprising adding peptide fragments covalently bonded to the hyaluronan.

5. The method of claim 1, further comprising adding peptide fragments covalently bonded to the at least one polycationic macromolecule.

6. The method of claim 1, further comprising adding peptide fragments covalently bonded to the dextran sulfate.

7. The method of claim 1, further comprising adding one or more biologically active agents.

8. The method of claim 7, wherein the biologically active agent is selected from the group consisting of growth factors, morphogens, hormones, cytotoxic agents, other therapeutic pharmaceutical compounds, extracellular matrix glycoproteins, proteoglycans, glycosaminoglycan, exendin-4, betacellulin, peptides that specifically bind an $\alpha 5\beta 1$ integrin, islet neogenesis-associated protein, islet neogenesis-associated protein fractions, islet neogenesis-associated protein derivatives, serum albumin, and combinations thereof.

9. The method of claim 1, wherein the dextran sulfate is of a low molecular weight of about 5 kilodaltons to about 40 kilodaltons.

10. The method of claim 1, wherein the dextran sulfate is of a high molecular weight of about 40 kilodaltons to about 1,000 kilodaltons.

11. The method of claim 1, wherein the dextran sulfate is sulfated from about 10% to about 13%.

12. The method of claim 1, wherein the dextran sulfate is sulfated from about 17% to about 22%.

13. The method of claim 1, wherein the dextran sulfate and the at least one polycationic macromolecule are at a charge ratio of $n^+/n^-$ equal to about 0.1, about 0.2, about 0.3, about 0.4, about 0.5, about 0.6, about 0.7, about 0.8, about 0.9, about 1.0, about 2.0, about 3.0, about 4.0, about 5.0, about 6.0, about 7.0, or about 8.0.

14. The method of claim 1, wherein the at least one polycationic macromolecule comprises chitosan.

15. The method of claim 14, wherein the chitosan is deactylated to at least 90%.

16. The method of claim 1, wherein the hybrid gel composition has a Young's modulus of about 0.5 kiloPascals to about 60 kiloPascals.

17. The method of claim 1, wherein the solvating fluid has an osmolarity of about 255 mOsmol/L to about 300 mOsmol/L.

18. The method of claim 1, wherein the solvating fluid comprises at least one dissolved polyanionic macromolecule, ½ normal saline, and glycerol phosphate.

* * * * *

SEQUENCE LISTING

```
<160> NUMBER OF SEQ ID NOS: 35

<210> SEQ ID NO 1
<211> LENGTH: 175
<212> TYPE: PRT
<213> ORGANISM: Homo sapiens

<400> SEQUENCE: 1

Met Leu Pro Pro Met Ala Leu Pro Ser Val Ser Trp Met Leu Leu Ser
1               5                   10                  15

Cys Leu Met Leu Leu Ser Gln Val Gln Gly Glu Pro Gln Arg Glu
            20                  25                  30

Leu Pro Ser Ala Arg Ile Arg Cys Pro Lys Gly Ser Lys Ala Tyr Gly
        35                  40                  45

Ser His Cys Tyr Ala Leu Phe Leu Ser Pro Lys Ser Trp Thr Asp Ala
    50                  55                  60

Asp Leu Ala Cys Gln Lys Arg Pro Ser Gly Asn Leu Val Ser Val Leu
65                  70                  75                  80

Ser Gly Ala Glu Gly Ser Phe Val Ser Ser Leu Val Lys Ser Ile Gly
                85                  90                  95

Asn Ser Tyr Ser Tyr Val Trp Ile Gly Leu His Asp Pro Thr Gln Gly
            100                 105                 110

Thr Glu Pro Asn Gly Glu Gly Trp Glu Trp Ser Ser Ser Asp Val Met
        115                 120                 125

Asn Tyr Phe Ala Trp Glu Arg Asn Pro Ser Thr Ile Ser Ser Pro Gly
    130                 135                 140
```

His Cys Ala Ser Leu Ser Arg Ser Thr Ala Phe Leu Arg Trp Lys Asp
145                 150                 155                 160

Tyr Asn Cys Asn Val Arg Leu Pro Tyr Val Cys Lys Phe Thr Asp
                165                 170                 175

<210> SEQ ID NO 2
<211> LENGTH: 14
<212> TYPE: PRT
<213> ORGANISM: Homo sapiens

<400> SEQUENCE: 2

Ile Gly Leu His Asp Pro Thr Gln Gly Thr Glu Pro Asn Gly
1               5                   10

<210> SEQ ID NO 3
<211> LENGTH: 14
<212> TYPE: PRT
<213> ORGANISM: Pan troglodytes

<400> SEQUENCE: 3

Ile Gly Leu His Asp Pro Thr Gln Gly Ser Glu Pro Asp Gly
1               5                   10

<210> SEQ ID NO 4
<211> LENGTH: 14
<212> TYPE: PRT
<213> ORGANISM: Mesocricetus auratus

<400> SEQUENCE: 4

Ile Gly Leu His Asp Pro Ser His Gly Thr Leu Pro Asn Gly
1               5                   10

<210> SEQ ID NO 5
<211> LENGTH: 14
<212> TYPE: PRT
<213> ORGANISM: Mus musculus

<400> SEQUENCE: 5

Ile Gly Leu His Asp Pro Thr Met Gly Gln Gln Pro Asn Gly
1               5                   10

<210> SEQ ID NO 6
<211> LENGTH: 14
<212> TYPE: PRT
<213> ORGANISM: Rattus norvegicus

<400> SEQUENCE: 6

Ile Trp Leu His Asp Pro Thr Met Gly Gln Gln Pro Asn Gly
1               5                   10

<210> SEQ ID NO 7
<211> LENGTH: 14
<212> TYPE: PRT
<213> ORGANISM: Bos taurus

<400> SEQUENCE: 7

Ile Gly Leu His Asp Pro Thr Glu Gly Ser Glu Pro Asp Ala
1               5                   10

<210> SEQ ID NO 8
<211> LENGTH: 14
<212> TYPE: PRT
<213> ORGANISM: Canis familiaris

<400> SEQUENCE: 8

Met Gly Leu His Asp Pro Thr Glu Gly Tyr Glu Pro Asn Ala
1               5                   10

<210> SEQ ID NO 9
<211> LENGTH: 14
<212> TYPE: PRT
<213> ORGANISM: Ovis aries

<400> SEQUENCE: 9

Ile Gly Leu His Asp Pro Thr Glu Gly Ser Glu Pro Asn Ala
1               5                   10

<210> SEQ ID NO 10
<211> LENGTH: 14
<212> TYPE: PRT
<213> ORGANISM: Homo sapiens

<400> SEQUENCE: 10

Ile Gly Leu His Asp Pro Lys Lys Asn Arg Arg Trp His Trp
1               5                   10

<210> SEQ ID NO 11
<211> LENGTH: 14
<212> TYPE: PRT
<213> ORGANISM: Homo sapiens

<400> SEQUENCE: 11

Ile Gly Leu His Asp Pro Lys Lys Asn Arg Arg Trp His Trp
1               5                   10

<210> SEQ ID NO 12
<211> LENGTH: 14
<212> TYPE: PRT
<213> ORGANISM: Rattus norvegicus

<400> SEQUENCE: 12

Ile Gly Leu His Asp Pro Lys Asn Asn Arg Arg Trp His Trp
1               5                   10

<210> SEQ ID NO 13
<211> LENGTH: 14
<212> TYPE: PRT
<213> ORGANISM: Mus musculus

<400> SEQUENCE: 13

Thr Gly Leu His Asp Pro Lys Arg Asn Arg Arg Trp His Trp
1               5                   10

<210> SEQ ID NO 14
<211> LENGTH: 14
<212> TYPE: PRT
<213> ORGANISM: Mus musculus

<400> SEQUENCE: 14

Thr Gly Leu His Asp Pro Lys Ser Asn Arg Arg Trp His Trp
1               5                   10

<210> SEQ ID NO 15
<211> LENGTH: 14
<212> TYPE: PRT
<213> ORGANISM: Mesocricetus auratus

<400> SEQUENCE: 15

Ile Gly Leu His Asp Pro Lys Asn Asn Arg Arg Trp His Trp
1               5                   10

<210> SEQ ID NO 16
<211> LENGTH: 14
<212> TYPE: PRT
<213> ORGANISM: Rattus norvegicus

<400> SEQUENCE: 16

Ile Trp Leu His Asp Pro Thr Met Gly Gln Gln Pro Asn Gly
1               5                   10

<210> SEQ ID NO 17
<211> LENGTH: 14
<212> TYPE: PRT
<213> ORGANISM: Rattus norvegicus

<400> SEQUENCE: 17

Ile Gly Leu His Asp Pro Thr Leu Gly Gly Glu Pro Asn Gly
1               5                   10

<210> SEQ ID NO 18
<211> LENGTH: 14
<212> TYPE: PRT
<213> ORGANISM: Rattus norvegicus

<400> SEQUENCE: 18

Ile Gly Leu His Asp Pro Thr Leu Gly Gln Glu Pro Asn Arg
1               5                   10

<210> SEQ ID NO 19
<211> LENGTH: 14
<212> TYPE: PRT
<213> ORGANISM: Mus musculus

<400> SEQUENCE: 19

Ile Gly Leu His Asp Pro Thr Met Gly Gln Gln Pro Asn Gly
1               5                   10

<210> SEQ ID NO 20
<211> LENGTH: 14
<212> TYPE: PRT
<213> ORGANISM: Mus musculus

<400> SEQUENCE: 20

Ile Gly Leu His Asp Pro Thr Leu Gly Ala Glu Pro Asn Gly
1               5                   10

<210> SEQ ID NO 21
<211> LENGTH: 14
<212> TYPE: PRT
<213> ORGANISM: Mus musculus

<400> SEQUENCE: 21

Ile Gly Leu His Asp Pro Thr Leu Gly Tyr Glu Pro Asn Arg
1               5                   10

<210> SEQ ID NO 22
<211> LENGTH: 14
<212> TYPE: PRT
<213> ORGANISM: Rattus norvegicus

```
<400> SEQUENCE: 22

Ile Gly Leu His Asp Pro Thr Leu Gly Gln Glu Pro Asn Arg
1               5                   10

<210> SEQ ID NO 23
<211> LENGTH: 14
<212> TYPE: PRT
<213> ORGANISM: Mesocricetus auratus

<400> SEQUENCE: 23

Ile Gly Leu His Asp Pro Thr Leu Gly Gln Glu Pro Asn Gly
1               5                   10

<210> SEQ ID NO 24
<211> LENGTH: 14
<212> TYPE: PRT
<213> ORGANISM: Homo sapiens

<400> SEQUENCE: 24

Ile Gly Leu His Asp Pro Thr Gln Gly Ser Glu Pro Asp Gly
1               5                   10

<210> SEQ ID NO 25
<211> LENGTH: 14
<212> TYPE: PRT
<213> ORGANISM: Mus musculus

<400> SEQUENCE: 25

Ile Gly Leu His Asp Leu Ser Leu Gly Ser Leu Pro Asn Glu
1               5                   10

<210> SEQ ID NO 26
<211> LENGTH: 14
<212> TYPE: PRT
<213> ORGANISM: Bos taurus

<400> SEQUENCE: 26

Ile Gly Leu His Asp Pro Thr Glu Gly Ser Glu Ala Asn Ala
1               5                   10

<210> SEQ ID NO 27
<211> LENGTH: 14
<212> TYPE: PRT
<213> ORGANISM: Mesocricetus auratus

<400> SEQUENCE: 27

Ile Gly Leu His Asp Pro Ser His Gly Thr Leu Pro Asn Gly
1               5                   10

<210> SEQ ID NO 28
<211> LENGTH: 14
<212> TYPE: PRT
<213> ORGANISM: Homo sapiens

<400> SEQUENCE: 28

Ile Gly Leu His Asp Pro Gln Lys Arg Gln Gln Trp Gln Trp
1               5                   10

<210> SEQ ID NO 29
<211> LENGTH: 14
<212> TYPE: PRT
<213> ORGANISM: Mus musculus
```

```
<400> SEQUENCE: 29

Ile Gly Leu His Asp Pro Gln Lys Lys Gln Leu Trp Gln Trp
1               5                   10

<210> SEQ ID NO 30
<211> LENGTH: 14
<212> TYPE: PRT
<213> ORGANISM: Pan troglodytes

<400> SEQUENCE: 30

Ile Gly Leu His Asp Pro Thr Gln Gly Ser Glu Pro Asp Gly
1               5                   10

<210> SEQ ID NO 31
<211> LENGTH: 14
<212> TYPE: PRT
<213> ORGANISM: Bos taurus

<400> SEQUENCE: 31

Ile Gly Leu His Asp Pro Thr Glu Gly Ser Glu Pro Asp Ala
1               5                   10

<210> SEQ ID NO 32
<211> LENGTH: 14
<212> TYPE: PRT
<213> ORGANISM: Canis familiaris

<400> SEQUENCE: 32

Met Gly Leu His Asp Pro Thr Glu Gly Tyr Glu Pro Asn Ala
1               5                   10

<210> SEQ ID NO 33
<211> LENGTH: 14
<212> TYPE: PRT
<213> ORGANISM: Ovis aries

<400> SEQUENCE: 33

Ile Gly Leu His Asp Pro Thr Glu Gly Ser Glu Pro Asn Ala
1               5                   10

<210> SEQ ID NO 34
<211> LENGTH: 15
<212> TYPE: PRT
<213> ORGANISM: Homo sapiens

<400> SEQUENCE: 34

Ile Gly Leu His Asp Pro Thr Gln Gly Thr Glu Pro Asn Gly Glu
1               5                   10                  15

<210> SEQ ID NO 35
<211> LENGTH: 15
<212> TYPE: PRT
<213> ORGANISM: Homo sapiens

<400> SEQUENCE: 35

Trp Ile Gly Leu His Asp Pro Thr Gln Gly Thr Glu Pro Asn Gly
1               5                   10                  15
```